United States Patent [19]
McGee et al.

[11] Patent Number: 6,090,932
[45] Date of Patent: Jul. 18, 2000

[54] METHOD OF PREPARATION OF KNOWN AND NOVEL 2'-MODIFIED NUCLEOSIDES BY INTRAMOLECULAR NUCLEOPHILIC DISPLACEMENT

[75] Inventors: Danny P. McGee, Boulder; Wolfgang A. Pieken, Longmont; David P. Sebesta, Boulder, all of Colo.; Yansheng Zhai, Palo Alto, Calif.

[73] Assignee: Proligo LLC, Boulder, Colo.

[21] Appl. No.: 08/732,283

[22] PCT Filed: May 25, 1995

[86] PCT No.: PCT/US95/06641

§ 371 Date: Oct. 30, 1996

§ 102(e) Date: Oct. 30, 1996

[87] PCT Pub. No.: WO95/35102

PCT Pub. Date: Dec. 28, 1995

Related U.S. Application Data

[63] Continuation-in-part of application No. PCT/US95/06641, May 25, 1995, which is a continuation-in-part of application No. 08/264,029, Jun. 22, 1994, abandoned.

[51] Int. Cl.$^7$ .......................... C07H 21/04; C07H 19/00; C07D 487/00
[52] U.S. Cl. ................. 536/25.3; 536/22.1; 536/23.1; 536/25.31; 536/25.32; 536/25.33; 536/25.34; 536/26.7; 536/26.8; 536/4.1; 544/263
[58] Field of Search ................... 536/26.7, 26.8, 536/23.1, 22.1, 25.31, 25.32, 25.33, 25.34, 4.1; 544/263

[56] References Cited

U.S. PATENT DOCUMENTS

| | | |
|---|---|---|
| 4,291,024 | 9/1981 | Turcotte . |
| 5,093,232 | 3/1992 | Urdea et al. . |
| 5,118,800 | 6/1992 | Smith et al. . |
| 5,118,802 | 6/1992 | Smith et al. . |
| 5,200,514 | 4/1993 | Chu . |
| 5,270,163 | 12/1993 | Gold et al. . |
| 5,420,276 | 5/1995 | Norbeck . |
| 5,466,786 | 11/1995 | Buhr et al. . |
| 5,576,429 | 11/1996 | Johansson . |

FOREIGN PATENT DOCUMENTS

| | | |
|---|---|---|
| 0 453 247 A2 | 10/1991 | European Pat. Off. . |
| 25 31 257 | 1/1976 | Germany . |
| WO 91/06556 | 5/1991 | WIPO . |
| WO 91/10671 | 7/1991 | WIPO . |
| WO 91/13900 | 9/1991 | WIPO . |
| WO 94/13789 | 6/1994 | WIPO . |
| WO 95/24185 | 5/1995 | WIPO . |

OTHER PUBLICATIONS

Aurup et al. (1992) Biochemistry 31:9636.
Bernet and Vasella (1983) Tetrahedron Letters 24:5491.
Caron and Sharpless (1985) J. Org. Chem. 50:1557.
Englisch and Gauss (1991) Angew. Chem. Int. Ed. Engl. 30:613.
Finan and Kishi (1982) Tetrahedron Letters 23:2719.
Guschlbauer et al. (1977) Nucleic Acids Research 4:1933.
Huryn and Okabe (1992) Chemical Reviews 92:1745.
Johnson et al. (1979) Tetrahedron Letters 45:4343.
Jung and Jung (1989) Tetrahedron Letters 30:6637.
Knapp et al. (1987) Tetrahedron Letters 28:5399.
Ludwig and Eckstein (1989) J. Org. Chem. 54:631.
Ma et al. (1982) J. Org. Chem. 47:1378.
McCombie et al. (1985) Tetrahedron Letters 26:6301.
McCombie et al. (1989) Tetrahedron Letters 30:7029.
McCombie et al. (1987) Tetrahedron Letters 28:383.
Minami et al. (1982) J. Am. Chem. Soc. 104:1109.
Nishikubo et al. (1981) Tetrahedron Letters 22:3873.
Nicolaou and Uenishi (1982) J. Chem. Soc., Chem. Commun. 1292.
Padwa et al. (1991) J. Org. Chem. 56:3556.
Paolella et al. (1992) EMBO J. 11:1913.
Pieken et al. (1991) Science 253:314.
Roush and Brown (1983) J. Org. Chem. 48:5093.
Roush et al. (1983) Tetrahedron Letters 24:1377.
Roush and Adam (1985) J. Org. Chem. 50:3752.
Roush and Brown (1982) J. Org. Chem. 47:1371.
Schubert et al. (1986) Liebigs Ann. Chem. 12:2009.
Tronchet et al. (1990) Tetrahedron Letters 31:531.
Tronchet et al. (1988) Nucleosides & Nucleotides 7:249.
Tuerk and Gold (1990) Science 249:505.
Verheyden et al. (1971) J. Org. Chem. 36:250.
Viti (1982) Tetrahedron Letters 23:4541.
Schmit (1994) Synlett 4:241.
Warshaw et al. (1990) J. Med. Chem. 33:1663.
Mikhailopulo et al. (1993) Liebigs Ann. Chem. pp. 513–519.
Buchanan and Clark (1979) Carbohydrate Res. 68:331–341.
Shibuya and Ueda (1980) Chem. Pharm. Bull. 28:939–946.
Wagner et al. (1991) Nucleic Acids Research 19:5965–5971.
Warshaw and Watanabe (1990) J. Med. Chem. 33:1663–1666.

*Primary Examiner*—James O Wilson
*Attorney, Agent, or Firm*—Swanson & Bratschun LLC

[57] ABSTRACT

A method for the preparation of 2'-modified nucleosides is provided. The method comprises a novel intramolecular nucleophilic displacement reaction. Included in the invention are novel 2'-modified pyrimidines and purines prepared according to the method of the invention, novel pyrimidines and purines bearing a 2',3' heterocyclic substituent and oligonucleotides containing said 2'-modified pyrimidines and purines. The 2'-modified nucleosides are useful as anti-viral and anti-neoplastic agents.

65 Claims, No Drawings

METHOD OF PREPARATION OF KNOWN AND NOVEL 2'-MODIFIED NUCLEOSIDES BY INTRAMOLECULAR NUCLEOPHILIC DISPLACEMENT

CROSS-REFERENCES TO RELATED APPLICATIONS

This application is a 371 of PCT/US95/06641, filed May 25, 1995, which is a continuation in part of Ser. No. 08/264,029, filed Jun. 22, 1994, now abandoned.

FIELD OF THE INVENTION

The present invention relates to methods of production of modified nucleosides. In particular, this invention includes novel methods for the production of 2'-modified pyrimidines. The preparation of such 2'-modified pyrimidines is accomplished in a novel intramolecular nucleophilic displacement reaction. Also included within the scope of this invention are certain novel 2'-modified pyrimidines prepared according to the method of the invention, and oligonucleotides containing such modified pyrimidine species. 2'-modified purines are also prepared by the method of the invention. The 2'-modified nucleosides are useful as antiviral and anti-neoplastic agents.

BACKGROUND OF THE INVENTION

Modified nucleotides and oligonucleotides have gained an important role in the development of pharmaceuticals over the last several years. For example, analogs of nucleosides and nucleotides have been employed as antiviral compounds. Oligonucleotides comprised of nucleotide analog building blocks have been used as inhibitors of gene translation. (See, Huryn and Okabe (1992) Chem. Rev. 92:1745–1788).

The recent discovery of oligonucleotide library screening technology has opened up an additional area for the pharmaceutical application of nucleotide analogs in oligonucleotides; as highly specific, high affinity inhibitors of protein function. See, e.g., U.S. Pat. No. 5,270,163 entitled, Nucleic Acid Ligands; and Tuerk and Gold (1990) Science 249:505–510. This technology is called SELEX, an acronym for Systematic Evolution of Ligands by Exponential Enrichment. SELEX can be carried out with libraries comprised of modified oligonucleotides to give ligands incorporating desired chemical functionalities (See, U.S. patent application Ser. No. 08/117,991, filed Sep. 8, 1993 and entitled "High Affinity Nucleic Acid Ligands containing Modified Nucleotides").

Stability against nuclease degradation is a concern in the field of oligonucleotide therapeutics. Oligodeoxynucleotides are often stabilized by the introduction of phosphorothioate internucleotidic linkages. (See, Huryn and Okabe (1992) Chem. Rev. 92:1745–1788; Englisch and Gauss (1991) Angew. Chem. 30:613–722).

Modification of the 2'-position of pyrimidines has also been shown to stabilize oligonucleotides against nuclease degradation. (See, Paolella et al. (1992) EMBO Journal 11:1913–1919; Pieken et al. (1991) Science 253:314–317.) Both 2'-amino and 2'-fluoro nucleotides have been used for this purpose. The 5'-triphosphate derivatives of these modified nucleotides are substrates for T7 RNA polymerase. (Aurup et al. (1992) Biochemistry 31:9636–9641.)

The introduction of modifications to the 2'-position of pyrimidine nucleosides is not a highly efficient process. Furthermore, current technology allows only for the preparation of a few select 2'-modified pyrimidines under harsh reaction conditions with low yield. (Verheyden et al. (1971) J. Org. Chem. 36:250–254.) A general reaction allowing facile preparation of a wide variety of novel and known 2'-modified pyrimidines has to date not been available.

To facilitate incorporation into oligonucleotide libraries, nucleotide analogs have to be prepared as the 5'-triphosphate derivatives. This is the form that is recognized as a substrate for DNA dependent RNA polymerases. Furthermore, analogs also have to be prepared as the phosphoramidites in order to be incorporated into the final oligonucleotide ligand by automated chemical synthesis.

There currently is no reliable method for the stereoselective preparation of ribo-2'-hydroxylaminopyrimidines. Derivatives of such compounds have not been described nor have these compounds been characterized. It has been reported that the $BH_3$ reduction of the oxime derivative of 2'-ketouridine affords mostly the 2'-hydroxylaminonucleosides of the arabino configuration. (Tronchet et al. (1990) Tetrahedron Lett. 31:531.) 2'-Halomethylpyrimidines are unknown. The 2'-aminopyrimidines are known compounds, however, they have never been prepared by an intramolecular introduction of the amino group. All previous procedures for synthesizing such compounds have proceeded through the 2'-azido precursor. (See, Verheyden et al. (1971) J. Org. Chem. 36:250–254.)

Cyclization reactions where a neighboring hydroxyl group is exploited as an anchor for a nucleophile which is then positioned to undergo cyclization with concomitant opening of an existing heterocycle have been observed in the opening of epoxyalcohols. (Jung and Jung (1989) Tetrahedron Lett. 30:6637–6640.)

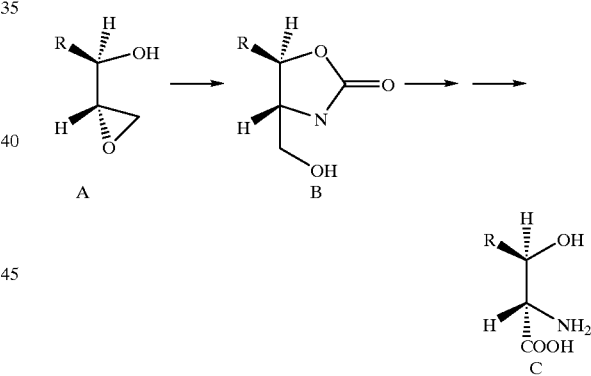

Oxidation and hydrolysis of B gave the desired β-hydroxy-amino acid C. It is not obvious that the crucial cyclization step should work analogously to open 2,2'anhydropyrimidines. Furthermore, the reported hydrolysis conditions are incompatible with nucleosides.

Other examples of similar intramolecular openings of epoxides have been reported. Roush et al. showed that a phenylcarbamate group can be directed to open an adjacent epoxide through the carbamate nitrogen or oxygen, depending on the reaction conditions. (See, Roush et al. (1983) J. Org. Chem. 48:5093; Roush and Adam (1985) J. Org. Chem. 50:3752.) Many additional examples of intramolecular nucleophilic epoxy alcohol ring openings by carbon, nitrogen, oxygen, and sulfur nucleophiles, as well as reductive openings and chelated additions by organometallic species have been reported. (See, Intramolecular carbon nucleophilic openings of epoxy alcohols: McCombie et al.

(1985) Tetrahedron Lett. 26:6301; McCombie et al. (1989) Tetrahedron Lett. 30:7029. Bicyclic products (e.g.; epoxides of cyclic olefins) Padwa et al. (1991) J. Org. Chem. 56:3556. Epoxy alcohol conversions by organometallic reagents: Me$_2$CuLi and/or Me$_3$Al: Roush et al. (1983) Tetrahedron Lett. 24:1377; Nishikubo and Kishi, (1981) Tetrahedron 37:3873; Johnson et al. (1979) Tetrahedron Lett. 20:4343. Ti(OiPr)$_4$-Mediated: Caron and Sharpless, (1985) J. Org. Chem. 50:1557. Reductive openings of epoxy alcohols: Red-Al/DiBAl: Finan and Kishi, (1982) Tetrahedron Lett. 23:2719; Viti (1982) Tetrahedron Lett. 23:4541; Katsuki et al. (1982) J. Org. Chem. 47:1378; Nicolaou and Uenishi (1982) J. Chem. Soc. Chem. Common. 1292. Intramolecular nitrogen nucleophilic openings of epoxy alcohols: N-Hydroxyl amides: Roush and Follows (1994) Tetrahedron Lett. 35:4935. Alkyl and acyl carbamates: Knapp et al. (1987) Tetrahedron Lett. 28:5399; McCombie and Nagabhushan, ibid 5395; Roush and Adam (1985) J. Org. Chem. 50:3752; Roush and Brown, ibid, (1982) 47:1371; Minami et al. (1982) J. Amer. Chem Soc. 104:1109. Bicyclic products (e.g.; epoxides of cyclic olefins): Schubert, et al. (1986) Liebigs Annalen der Chemie 2009. Intramolecular oxygen nucleophilic openings of epoxy alcohols: McCombie and Metz (1987) Tetrahedron Lett. 28:383; Roush et al. (1983) J. Org. Chem. 48:5093; Katsuki et al. (1982) J. Org. Chem. 47:1378. The opening of an epoxide by an adjacent trichloroacetimidate has been reported: Bernet and Vasella, (1983) Tet. Letters 24:5491–5494.

2'-O-Methyl ethers of nucleosides are known to occur in nature as minor components of transfer RNA. (R. H. Hall, "The Modified Nucleosides in Nucleic Acids." Columbia University Press, New York, N.Y., 1971). 2'-O-Alkyl substituted nucleosides have been used to stabilize oligonucleotides against chemical and enzymatic degradation (For example see E. DeClerq et al., FEBS Letters, 1972, 24, 137; H. Inoue et. al., FEBS Letters, 1987, 215, 327; A. M. Iribarren et. al., Proc. Natl. Acad. Sci. USA 1990, 87, 7747; G. Kawai et. al., Biochemistry 1992, 31, 1040.). 2'-O-Alkyl substitutents also can serve as removable protecting groups for the 2'-hydroxyl of ribonucleosides in oligonucleotide synthesis. (For example see K. Kikugawa et. al., Chem. Pharm. Bull. 1967, 16, 1110; H. Takaku et. al., J. Org. Chem. 1984, 49, 51; L. W. McLaughlin et. al., Synthesis, 1985, 322.).

2'-O-Alkyl nucleosides have been prepared by stannous chloride catalyzed reaction of free nucleosides and diazomethane followed by a tedious separation of alkylated isomers as described by M. J. Robins et. al., J. Org. Chem. 1974, 39, 1891. A further alkylation preceedure is described by D. Wagner et. al., J. Org. Chem. 1974, 39, 24. Where the free nucleosides uridine, cytidine and adenosine are alkylated by the reaction of a preformed 2',3'-O-dibutylstannylene nucleoside with alkyl halides to afford a mixture of 2'-O and 3'-O-alkylated products. Alternatively 2'-O-alkylated nucleosides have been obtained as the result of an exhaustive protection scheme of both the sugar and/or the heterocycle followed by selective alkylation of the free hydroxyl and removal of all the protecting groups. Notable is the use of the 5',3'-O-(tetraisopropyl-disiloxane) as described by H. Inoue et. al., Nucleic Acids Res. 1987, 15, 6131., V. A. Gladkaya et. al., Khim. Prir. Soedin, 1989, 4, 568; B. S. Sproat et. al., Nucleic Acids Res. 1989, 18, 41; T. Akiyama et. al., Bull. Chem. Soc. Jpn. 1990, 63, 3356. as well as tritylation for this purpose in Y. Furukawa et. al., Chem. Pharm. Bull. 1965, 13, 1273; E. Wagner et. al., Nucleic Acids Res. 1991, 19, 5965; K. Yamana et. al., Tet. Let. 1991, 32, 6347. 2,2'-Anhydropyrimidines of some common nucleosides are commercially available (Aldrich: anhydrouridine, anhydrocytidine) or are easily prepared by those skilled in the art (for example see K. K. Ogilvie et al., Can. J. Chem. 1969, 47,495; A. Hampton et. al., Biochemistry, 1966, 5, 2076.). 8,2'-Anhydropurines are easily prepared by those skilled in the art (For a Review of methods see J. G. Moffatt in "Nucleoside Analogues", R. T. Walker et. al., Eds., Plenum Publishing Corp. 1979). K. K. Ogilvie et al. (1972) Con. J. Chem. 50:2249

Metal alkoxides are commercially available and methods of preparation are known to those skilled in the art. Meant as an example but not limited to the following see Gelest Inc., Tullytown, Pa., 1994–95 cataloque; Johnson Matthey, ALPHA, Ward Hill, Pa., 1994–95 catalogue, Aldrich Inc. catalogue. All metal alkoxides listed are included herein by reference. They are easily made by reaction of the metal with an excess of alcohol with optional heating and activation of the metal (ie. I$_2$, HgX$_2$), or reaction of organometalic compounds with alcohols, or metal hydrides with alcohols, or metal halides with alcohols or alkoxides (Na, K, other monovalent cation salts) or alcoholysis of a metal alkoxide with an excess of a second alcohol.

SUMMARY OF THE INVENTION

The present invention includes a process for the production of 2'-substituted nucleosides. The facile introduction of a large variety of functionalities at the 2'-position is accomplished via an intramolecular nucleophilic displacement. 2'-substituted pyrimidines and purines can be made by this method.

The present invention also includes an improved process for preparing 2'-O-substituted nucleosides. In this aspect, the invention relates to a process whereby anhydronucleosides are converted by reaction with a metal (alkoxide)n; preferably where n is at least 2, to afford the 2'-O-alkyl ribonucleoside. The process is higher yielding and requires no separation of isomers, which is an improvement over the prior processes.

Included within the scope of this invention are 2'-modified nucleosides prepared according to the method of the present invention, phosphoramidites of the 2'-modified nucleosides, 5'-triphosphates of the 2'-modified nucleosides, and oligonucleotides comprised of at least one of such modified nucleosides. Nucleosides of the invention can be transformed into the corresponding 5'-diacylglycero- or dialkylglycerophosphate derivates for use as prodrugs. This invention further covers novel nucleosides, bearing a 2',3' fused heterocyclic substituent, prepared according to the method of the present invention.

The present invention also includes intramolecular functionalization of anhydronucleosides at other positions of the ribose ring.

The modified nucleosides of the invention are also useful as anti-viral and anti-neoplastic agents.

DETAILED DESCRIPTION OF THE INVENTION

A novel and general process is described herein which allows for the facile introduction of a broad variety of nucleophiles to the 2', 3', 5'-position of nucleosides. The preferred modification is at the 2'-position of nucleosides.

A generalized depiction of the reaction step that leads to the 2'-modified nucleosides is show below as follows:

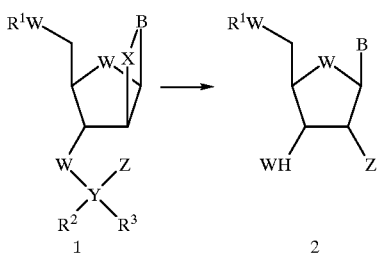

According to this reaction scheme:

B is a nucleobase;

W is independently selected from the group consisting of O, S, $CR^2_2$, $NR^2$, $PR^2$ and $POR^2$;

X is selected from the group consisting of O, S, NH, and $NR^4$;

Y is selected from the group consisting of a metal, C, Si, Se, S, B, Al, Sn, and P;

Z is selected from the group consisting of imidazole, Cl, F, H, $^2$H, $^3$H, OH, $NHOR^1$, $NHOR^5$, $NHNHR^5$, $NHR^5$, =NH, CHCN, $CHCl_2$, SH, $SR^5$, $CFH_2$, $CF_2H$, $CR^22Br$, $OR^4$;

$R^1$ is selected from the group consisting of H and an alcohol protecting group;

$R^2$ is selected from the group consisting of =O, =S, H, OH, $CCl_3$, $CF_3$, halide, optionally substituted $C_1$–$C_{20}$ alkyl (including cyclic, straight chain, and branched), alkenyl, aryl, $C_1$–$C_{20}$ acyl, benzoyl, $OR^4$ and esters;

$R^3$ is selected from the group consisting of =O, =S, OH, H, $CCl_3$, $CF_3$, halide, $C_1$–$C_{20}$ alkyl, alkenyl, aryl, benzoyl, esters, $OR^4$, omitted, and cyclopentadiene, cyclooctadiene, CO and trialkylphosphine if Y is metal;

$R^4$ is selected from the group consisting of an optionally substituted hydrocarbon ($C_1$–$C_{20}$ alkyl, $C_2$–$C_{20}$ alkenyl, $C_2$–$C_{20}$ alkynyl, and aryl), an optionally substituted heterocycle, nucleoside, carbohydrate, fluorescent label, and phosphate;

$R^5$ is selected from the group consisting of $R^2$, $R^4$, CN, $C(O)NH_2$, $C(S)NH_2$, $SO_2R^4$, amino acid, peptide and mixtures thereof.

Other obvious substitutions for components of this reaction scheme are also included within the scope of this invention, which is not limited to the specific, but rather the generalized formula of reaction.

In the preferred embodiments of the invention,

B is selected from the group consisting of a pyrimidine connected to X at the 2-position, a pyrimidine connected to X at the 6-position, and a purine connected to X at the 8-position;

W is O;

X is selected from the group consisting of O, S, and NH;

Y is selected from the group consisting of a metal, C, Si, B, Al, Sn, and P;

Z is selected from the group consisting of imidazole, H, $NHOR^1$, $NHOR^5$, $NHNHR^2$, $NHR^2$, =NH, SH, and $OR^4$;

$R^1$ is selected from the group consisting of H and an alcohol protecting group;

$R^2$ is selected from the group consisting of =O, =S, OH, H, $CCl_3$, $CF_3$, halide, $C_1$–$C_{20}$ alkyl, alkenyl, aryl, $C_1$–$C_{20}$ acyl, benzoyl, and ester;

$R^3$ is selected from the group consisting of =O, =S, H, $CCl_3$, $CF_3$, halide, $C_1$–$C_{20}$ alkyl, alkenyl, aryl, benzoyl, esters and omitted;

$R^4$ is selected from the group consisting of optionally substituted $C_1$–$C_{20}$ alkyl, $C_2$–$C_{20}$ alkenyl, $C_2$–$C_{20}$ alkynyl, and aryl; and $R^5$ is selected from the group consisting of $R^2$, $R^4$ and peptide.

For the purposes of this invention nucleobase will have the following definition. A nucleobase is a purine or pyrimidine base. Nucleobase includes all purines and pyrimidines currently known to those skilled in the art. Nucleobase includes uracil, cytosine, N4-protected cytosine, 4-thiouracil, isocytosine, 5-methyluracil (thymine), 5-substituted uracils, adenine, N6-protected adenine, guanine, N2-protected guanine 2,6-diaminopurine, halogenated purines as well as heterocycles meant to mimic the purine or pyrimidine ring, such as HNCNH. Preferably, the pyrimidine bases are connected to X at the 2 position (2,2'-anhydropyrimidines) or the 6 position (6,2'-anhydropyrimidines); the purine bases are connected to X at the 8 position (8,2'-anhydropurines) or X constitutes the N-3 of the purine (N3,2'-anhydropurines).

As used herein, optionally substituted hydrocarbon refers to groups which consist solely of carbon and hydrogen which may be substituted by groups containing atoms other than hydrogen and carbon. Examples of optionally substituted hydrocarbons are cyanoethyl, allyl, propargyl, methyl, ethyl, propyl, 4-amino butyl, phenyl, napthyl, nitrophenyl, methylphenyl and the like. It is understood that the various substituents must be compatible with standard chemical reactions as would be known by one of ordinary skill in the art.

In certain cases the reaction from 1 to 2 proceeds via the bicyclic intermediate 1a as shown below:

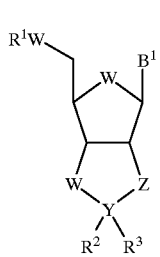

1a

This intermediate may be stable and consists generally of the same chemical functional groups for W, X, Y, Z, $R^1$, $R^2$, $R^3$, $R^4$, and B as described above, where such compounds are chemically possible.

The cyclization intermediates 1 and 1a as defined above are also included within the scope of this invention, as are all 2'-modified nucleosides 2 that are produced via the intramolecular reaction depicted above. Also included are phosphoramidites and 5'-triphosphates of compound 2, and oligonucleotides comprised of at least one residue consisting of 2. Nucleosides of compound 2 may be transformed by standard methods known to those skilled in the art to the corresponding 5'-diacylglycero- or dialkylglycerophosphate-derivatives for use as prodrugs, among other uses. These modified nucleosides are particularly interesting for antiviral applications. The diacylglycerophosphates of nucleosides and nonnucleosides have been used for modulation of pharmacokinetic behavior, modulation of bioavailability, and modulation of toxicity as described in U.S. Pat. No. 5,223,263 which is herein incorporated by reference. Derivatization of the novel nucleosides described in this application is expected to exert similar effects on activity as is true for the diacylglycerophosphates of known nucleoside antivirals such as DDC.

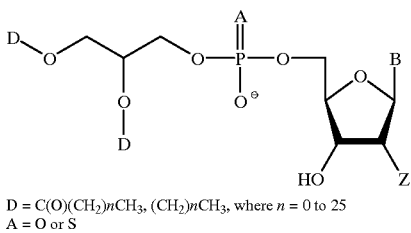

D = C(O)(CH$_2$)$_n$CH$_3$, (CH$_2$)$_n$CH$_3$, where $n$ = 0 to 25
A = O or S

The cyclization is achieved using bases such as sodium hydroxide, diazabicyclo [5.3.0] undecane (DBU), triethylamine (TEA), diisopropylethylamine (DIPEA), Cs$_2$CO$_3$, and the like. Preferably the base is DBU or TEA.

Introduction of a modifying group, which carries an activatable nucleophilic atom in the β-position to the 3'-oxygen of 5'-protected anhydronucleosides gives intermediates of the general formula 1. These intermediates serve as precursors that can undergo the stereospecific intramolecular introduction of the nucleophile Z to the 2'-position of the nucleoside. The initial cyclization step gives 2',3'-cyclic intermediates 1a. These can be stable compounds, that may have antiviral or anticancer properties. A preferred intermediate for the production of 2'-NH$_2$ modified nucleosides and triphosphates is the following:

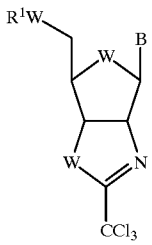

This reaction, and subsequent deprotection, proceeds under mild conditions. In many cases, the resulting 2'-modified nucleosides 2 are novel compounds. Where Z=NHOH, the heretofore unknown 2'deoxy,2'-N-hydroxylaminonucleosides 3 of the ribo-configuration are prepared. Where Z=halo methyl, the heretofore unknown 2'-deoxy,2'-halomethylnucleosides 4 are prepared. Modified nucleosides of the general formulas 3 and 4 are also included as part of this invention.

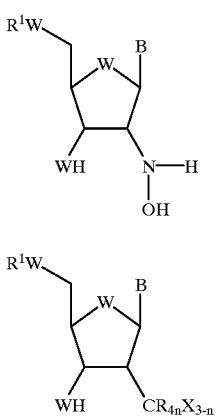

At the same time, this invention provides a significant improvement for the preparation of known compounds of the general formula 2. Such modified nucleosides prepared according to this invention may be transformed by standard methods known to those skilled in the art to the corresponding 5'-triphosphate derivatives. The corresponding mono- and diphosphates are also within the scope of the present invention. The nucleoside triphosphates may also be incorporated into oligonucleotides. In one embodiment, the triphosphates are incorporated by in vitro transcription using DNA dependent RNA polymerases. The nucleosides 2 may also be transformed to the suitably protected 3'-phosphoramidite derivatives by standard methods known to those skilled in the art for incorporation into oligonucleotides by automated solid phase synthesis.

In the performance of the process of the present invention, intermediate compound 1 is prepared according to procedures familiar to those skilled in the art. Experimental protocols for the preparation of several examples of intermediate compound 1 are described in the examples below. In the preferred embodiment of the present invention, the intramolecular nucleophilic reaction where compound 1 is converted to compound 2 is accomplished in the presence of Cs$_2$CO$_3$ and an alcohol. Alcohol protecting group R$^1$ includes tert-butyl diphenylsily (TBDPS), dimethoxytrityl (DMT) any other commonly employed protecting groups, and protecting groups derivatized with Polymeric and solid-phase supports.

Intermediate compound 1 may be prepared via a variety of processes. In the preferred embodiment, a variety of intermediate compound of formula 1 may be prepared from the intermediate compound 3'-O-carbonylimidazole-5'-O-tert-butyldiphenlysily-2-2'-anhydrouridine 5. Such intermediate compound 5 is useful for the introduction of activatable nucleophiles with the correct orientation for the intramolecular reaction of the present invention.

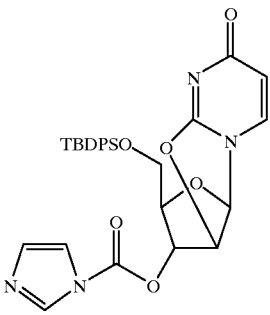

The invention further relates to a process for preparing compounds of the formula 2c which comprises reacting compounds of the formula 1c with a metal alkoxide M(OR$^4$)$_n$, wherein:

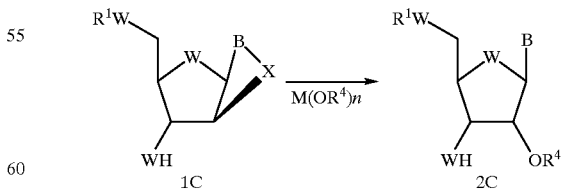

B is a nucleobase;
W is independently selected from the group consisting of S, O, CR$^2_2$, NR$^2$, pR$^2$, and POR$^2$;
X is selected from the group consisting of O, S, NH, and NR$^4$;

$R^1$ is selected from the group consisting of H and an alcohol protecting group;

$R^4$ is selected from the group consisting of optionally substituted hydrocarbon [($C_{1-19}$) alkyl, alkenyl, alkynyl, aryl)], optionally substituted heterocycle, nucleoside, fluorescent label, and phosphate.

M is a metal capable of forming a bis or higher alkoxide with $OR^4$ selected from the group consisting of Mg, Be, Sr, Ba, Th, Zr, Cr, Fe, Ni, Cu, Zn, Mn, Ca, Ce, Ti, Si, Sn, Pd, and the lanthanide series.

n is 2–6.

Alcohol protecting groups are known to those skilled in the art, and include, but are not limited to, trityl groups, substituted silyl groups, etc., H.

More specifically, a preferred embodiment of the invention relates to a process wherein the metal bis alkoxide is formulated with metals exhibiting a +2 oxidation state such as Mg, Ca and the like.

Another preferred embodiment is preparing compounds of formula 2c wherein R' is methyl, propyl, ethyl, butyl, pentyl or allyl.

Another preferred embodiment is the instance where compounds of formula 1c when Y=S are converted to compounds of formula 2c with B now signifying a 2-thiopyrimidine or an 8-thiopurine. Such compounds (2'-O-substituted 8-thiopurines and the like) may be desulferized by the use of certain reagents known to those in the art, for example Raney nickel, to give compounds of formula 2c where B=a purine unsubtituted at the 8 position.

Still another preferred embodiment is compounds of formula 1c wherein X=O,S and B=Uracil, Cytosine, Guanine, N2-protected Guanine, Adenine, N6-protected adenine.

The process of the present invention is depicted in the above scheme. The compounds of formula 1c are prepared by reaction of a preformed 2,2'-anhydropyrimidine or 8,2'-anhydropurine for example, with a protecting group such as dimethoxytrityl chloride or t-butyldiphenylchlorosilane and the like in a solvent such as DMF, pyridine, N-methylpyrrolidinone, dioxane, acetonitrile Triethyl amine, and the like or mixtures thereof, containing optional additives such as imidazole, dimethylaminopyridine. The mixture is stirred from 1–24 h between 10–50° C., preferably at room temperature. The reaction is evaporated in vacuo and the residue dissolved in an organic solvent such as ethyl acetate or dichloromethane and washed with dilute aqueous solutions of sodium bicarbonate and/or ammonium chloride. The organic phase is dried with, for example, magnesium or sodium sulfate and evaporated. The residue can be purified by chromatography on Silica gel to give compounds of formula 1c.

The compounds of formula 2c are prepared by reaction of compounds of formula 1c with a metal bis alkoxide using from 1–10 equivalents of metal alkoxide in a solvent such as DMF, DMSO, N-methylpyrrolidinone, acetonitrile and the like, preferably DMF. The mixture is heated from 4–24 h between 25–150° C., preferably at 100° C. The solvents are removed under vacuum and the residue may be purified by simple extraction procedures or optionally purified by chromatography on silica gel to afford compounds of formula 2c.

In the instance where a compound of formula 1c (Y=S) is used to afford a compound of formula 2c (with resultant thiopyrimidine or thiopurine as B) the purine or pyrimidine may be desulferized using reagents known to those skilled in the art, for example refluxing with ethanolic Raney nickel, to afford the compounds of formula 2c where the thio of the purine or pyrimidine has been replaced by a hydrogen.

As shown in the scheme below, various anhydropyrimidines and anhydropurine nucleosides are likely substrates for the method of the invention.

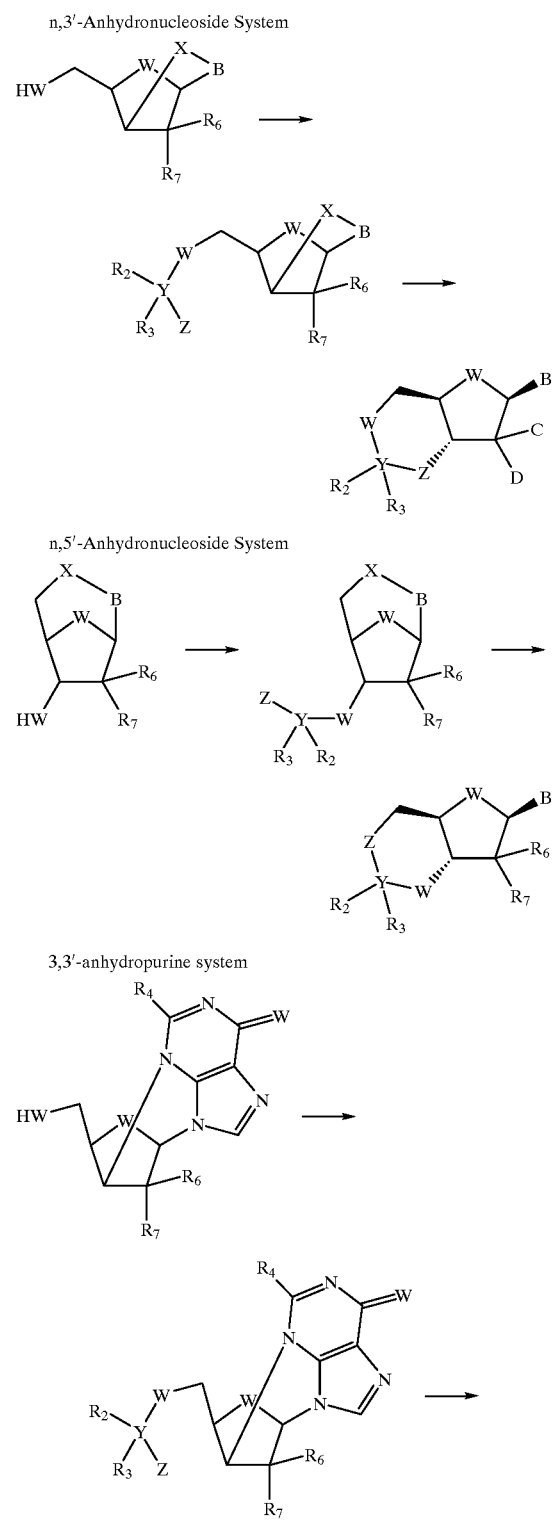

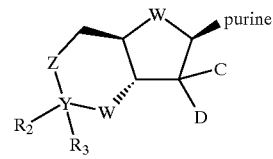

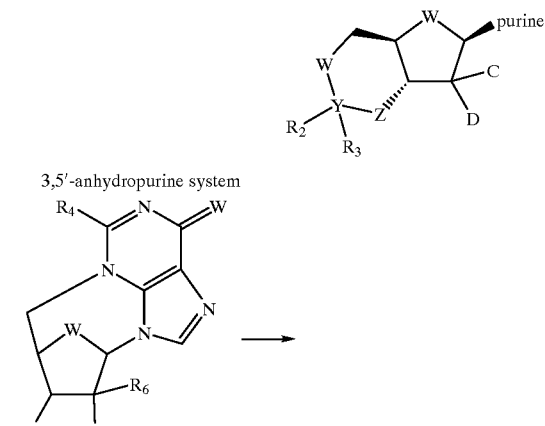

3,5'-anhydropurine system

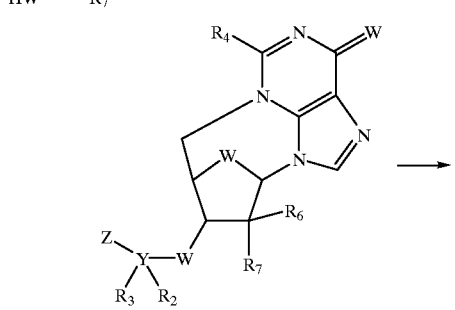

The invention is as broadly described above, and should not be considered to be limited by the breadth of the specific examples below, which serve to illustrate the invention with respect to specific embodiments.

EXAMPLE 1

Preparation of 2'-deoxy-2'-aminouridine

Uridine is converted to 2,2'-anhydrouridine 6 by standard methodology. (Verheyden et al. (1971) J. Org. Chem. 36:250–254.) Protection of the primary 5'-hydroxyl group gives the 5'-O-(4,4'-dimethoxytrityl) 2,2'-anhydrouridine 7. Intermediate 7 is reacted with trichloroacetonitrile to give the 3'-imidate 8. Typically, the protected anhydrouridine 7 is directly converted to the 2',3'-oxazoline 9. This compound is then hydrolyzed to either the 5'-(4,4'-dimethoxytrityl)-2'-amino-2'-deoxyuridine 10 by treatment with base, or to the fully deprotected 2'-amino-2'-deoxyuridine 11 by treatment with acid. The intermediate oxazole 9 can also be converted to the respective cytidine derivative 12. All NMR where measured at 300 Mhz in DMSO.

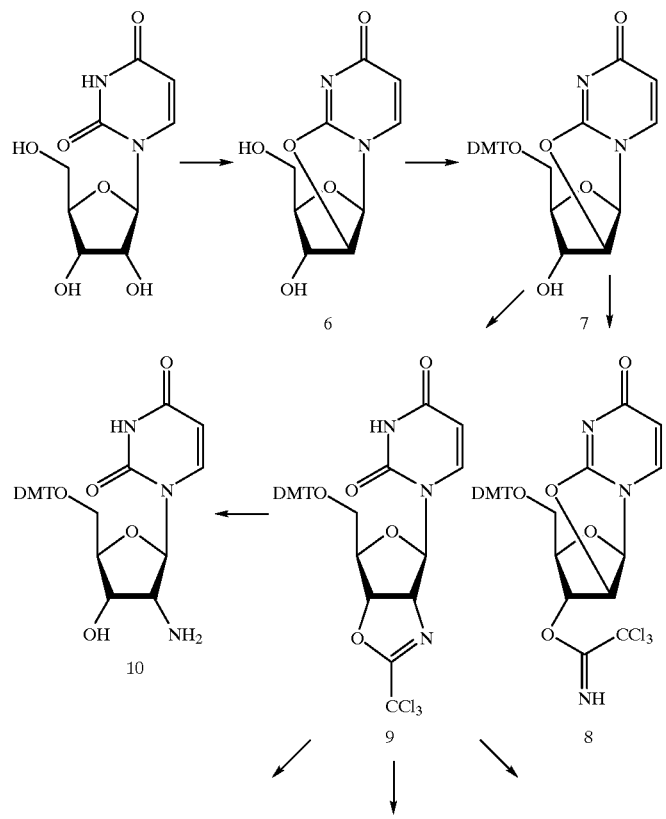

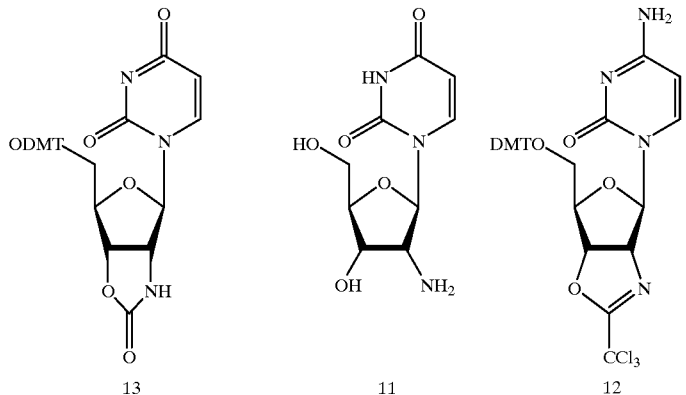

5'-O-(4,4'-Dimethoxytrityl)-2,2'-anhydro-1-(β-D arabinofuranosyl)uracil(7).

A suspension of 2,2'-O-anhydrouridine (10.1 g, 0.045 moles) and dimethoxytrityl chloride (17.5 g, 1.1 eq) in pyridine (100 mL) and catalytic DMAP (50 mg) was stirred 16 hrs at RT prior to evaporation. The residue was taken up in dichlorometlhane, washed with water, followed dil, sodium bicarbonate. The organic phase was dried with magnesium sulfate and evaporated. The resulting foam was purified on silica gel eluting with 0–20% methanol/ethyl acetate to afford the desired material as a foam 13.3 g, 56% yield. NMR (DMSO-$d_6$) Δ 2.81 and 2.85 (ABX, 2 H, H5',5", $J_{ab}$=10.2 Hz, $J_{ax}$=4.2 Hz, $J_{bx}$=1 Hz), 3.73 (s, 6 H, OCH$_3$), 4.22 (m, 1 H, H3'), 4.31 (m, 1 H, H4'), 5.21 (d, 1 H, H2', J=5.7 Hz), 5.89 (d, 1 H, H5, J=7.4 Hz), 5.96 (d, 1 H, 3'—OH, J=4.4 Hz) 6.33 (d, 1 H, H1', J=5.6 Hz), 6.84, 7.16, 7.28 (m, 13 H, DMT), 7.96 (d, 1 H, H6, J=7.4). Anal. calcd for $C_{30}H_{28}N_2O_7/0.5H_2O$: C,67.03; H,5.43; N,5.21; found: C, 67.02; H, 5.55; N, 4.99.

5'-O-(4,4'-dimethoxytrityl)-3'-O-(trichloroacetimidate)-2,2'-anhydro-1-(β-D-arabinofuranosyl)uracil (8).

To a solution of 5'-dimethoxytrityl anhydrouridine 7 (1.0 g, 1.9 mmoles) in dioxane (5 mL) and trichloroacetonitrile (1 mL) was added sodium hydride (40 mg, 60% in mineral oil) and the reaction was stirred 16 h at room temperature prior to evaporation. The residue was purified on silica gel eluting with 10% methanol/dichloromethane to afford imidate 8 as an orange foam (500 mg). NMR (DMSO-$d_6$) Δ 2.91 and 3.12 (ABX, 2 H, H5',5", $J_{ax}$=4.4 Hz, $J_{bx}$=6.3 Hz, $J_{ab}$=10.4 Hz), 3.73 (s, 6 H, OCH$_3$), 4.49 (s, 1 H, H4'), 5.49 (s, 1 H, H3'), 5.55 (d, 1 H, H1', J=5.7 Hz), 5.95 (d, 1 H, H6, J=7.5), 6.85 and 7.13–7.29 (m, 13 H, DMT), 7.95 (d, 1 H, H6, J=7.5 Hz), 10.0 (s, 1 H, NH).

5'-O-(4,4'-dimethoxytrityl)-2'-N,3'-O-(2-trichloromethyloxazolino)-2'-deoxy-1-(β-D-ribofuranosyl)uracil (9).

A mixture of 5'-dimethoxytrityl-2,2'-anhydrouridine 7 (1.1 g, 2.1 mmoles) in neat trichloroacetnitrile (5 mL) and sodium hydride (40 mg, 0.5 eq, 60% in mineral oil) was heated at 90° C. for 16 h prior to evaporation. The dark residue was purified on silica gel eluting with 10% methanol/dichloromethane containing 1% triethyl amine to afford the desired material 9 as a yellow foam (600 mg). NMR (DMSO-$d_6$) Δ 3.16 and 3.48 (ABX, 2 H, H5' and H5"), 3.72 (s, 6 H, OCH$_3$), 4.14 (m, 1 H, H4'), 5.29 (dd, 1 H, H2', $J_{2',3'}$=8.3 Hz, $J_{2',1}$=1.9 Hz), 5.43 (dd, 1 H, H3', $J_{3',4'}$=4.5 Hz), 5.65 (d, 1 H, H5, $J_{5,6}$=8 Hz), 5.92 (d, 1 H, H1', $J_{1',2'}$=1.8 Hz), 6.86, 7.2, 7.38 (m, 13 H, DMT), 7.84 (d, 1 H, H6, $J_{5,6}$=8.1 Hz), 11.44 (s, 1 H, NH). C13-NMR (75 MHz) 164.24, 162.44, 159.05, 151.09, 145.67, 144.56, 136.07, 130.47, 130.32, 128.56, 128.33, 127.45, 113.83, 102.37, 93.88, 87.16, 86.79, 86.15, 76.87, 64.31, 55.28, 55.24, 52.05. Anal. calcd for $C_{32}H_{28}N_3O_7Cl_3$: C,57.11; H,4.19; N,6.24; Cl,15.80; found: C,57.43; H,4.78; N,6.08; Cl,15.44.

5'-O-Dimethoxytrityl-2'-amino-2'-deoxyuridine (10).

Dimethoxytrityl oxazoline 9 (1.5 g, 2.23 mmoles) in dioxane (30 mL) to which is added sodium hydroxide (109 mg in 1 mL water) is refluxed 10 h and then evaporated. The residue was partitioned between water and dichloromethane, dried with magnesium sulfate and evaporated. It was purified on silica gel eluting with 5–10% methanol/dichloromethane to afford first 5'-O-dimethoxytrityl-2'-N,3'-O-(oxazolin-2-one)-2'-deoxyuridine (13) as a yellow foam (900 mg, 58% yield). NMR (DMSO-$d_6$) 3.15 and 3.36 (ABX, 2 H, H5',5"), 3.7 (s, 6 H, OCH$_3$), 4.20 (m, 1 H, H4'), 4.51 (d, 1 H, H3'), 4.98 (q, 1 H, H2'), 5.59 (d, 1 H, J=8 Hz, H5), 5.76 (br s, 2 H, H1', OH), 6.67 and 7.23–7.4 (m, 13 H, DMT), 7.68 (d, 1 H, H6, J=8 Hz), 8.27 (s, 1 H, 2'-NH), 11.47 (s, 1 H, NH). This was followed by the free amino compound 10 (95 mg) as a foam. NMR (DMSO-$d_6$) Δ 3.18 and 3.22 (ABX, 2 H, H5',5"), 3.38 (m, 1 H, H2'), 3.7 (s, 6 H, OCH$_3$), 3.97 (m, 2 H, H3', H4'), 5.41 (d, 1 H, H5, J=8 Hz), 5.68 (d, 1 H, H1', J=7.2 Hz), 6.88 and 7.23–7.39 (m, 13 H, DMT), 7.64 (d, 1 H, H6, J=8.1 Hz). This product was identical with material prepared via the traditional 2'-azido route.

2'-Amino-2'-deoxyuridine (11):

Dimethoxytrityl oxazoline 9 (100 mg) was treated with 80% aqueous acetic acid for 16 h at room temperature and then evaporated. The residue was co-evaporated with methanol and then partitioned between dichloromethane/water, the water evaporated and the residue dried under vacuum to afford 11 as a glass (50 mg). As sample was crystallized from MEOH MP 197–199° C. (uncorrected). The product data was identical to published reports.

EXAMPLE 2

Preparation of 2'-Hydroxylaminouridine derivatives

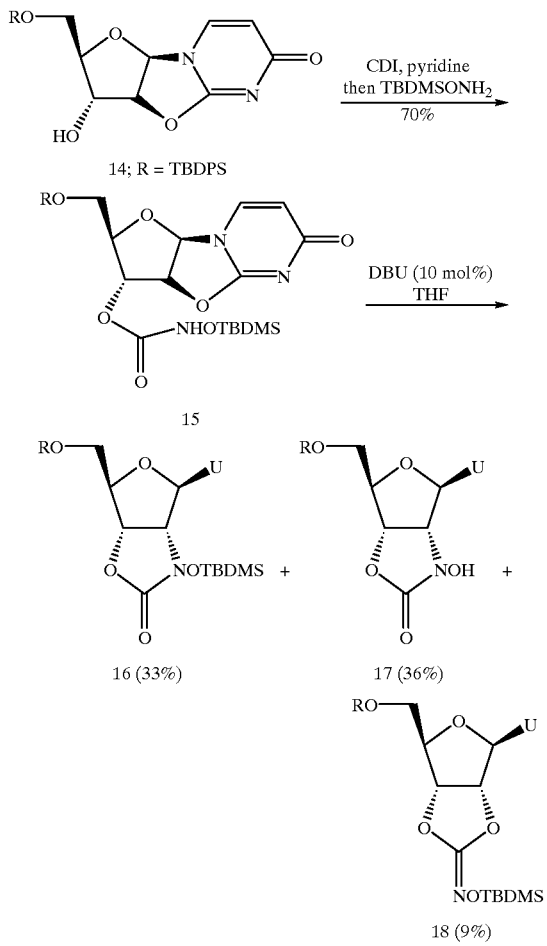

In this example, 5'-O-tert-butyldiphenylsilyl-2,2'-anhydrouridine (14) is converted to the hydroxylamine derivative 15 by sequential treatment with carbonyldiimidazole and TBDMSONH$_2$. This intermediate containing the latent nucleophile is exposed to catalytic amounts of base (DBU) and this results in conversion to three ring-opened nucleoside products 16, 17, and 18. 2'-Hydroxylamino uridine derivatives 16 and 17 (which likely results from desilylation of 16) are a result of N-selective nucleophilic attack, while uridine derivative 18 derives from O-selective nucleophilic attack.

5'-O-tert-Butyldiphenylsilyl-2,2'-anhydrouridine (14):

To a stirred slurry of 35 g (0.15 mol) of 2,2'-anhydrouridine in 300 mL of anyhdrous pyridine and 135 mL anhydrous DMF was added 40.1 mL (0.15 mol) of tert-butylchlorodiphenylsilane dropwise via syringe over 5 min. Upon stirring overnight, all solids went into solution and the reaction mixture was concentrated in vacuo. The crude residue was dissolved in 800 mL CH$_2$Cl$_2$ and the cloudy solution washed with 1.2 L NaHCO$_3$ solution, dried over Na$_2$SO$_4$ and concentrated. The residue was recrystallized from EtOAc to give 45 g (63%) of product as a white chalk. Concentration of the mother liquor afforded an additional 4.8 g (6.5%) of crystalline product. 14: $^1$H NMR (300 MHz, CDCl$_3$) d 7.62–7.51 (m, 4H), 7.48–7.30 (m, 7H), 6.17 (d, J=5.8 Hz, H1'), 6.00 (d, J=7.5 Hz, H5), 5.41 (dd, J=5.9, 1.8 Hz, H2'), 5.26 (d, J=4.8 Hz, OH), 4.61 (m, H3'), 4.26 (dd, J=10.0, 5.2 Hz, H4'), 3.62 (dd, J=11.4, 5.1 Hz, H5'), 3.55 (dd, J=11.4, 6.1 Hz, H5'), 0.98 (s, 9H). $^{13}$C NMR (75 MHz, DMSO-d6) d 172.24, 160.68, 137.9, 136.0, 135.9, 133.6, 133.4, 130.9, 128.9, 109.6, 90.2, 89.4, 87.9, 74.7, 63.2, 60.3, 26.8, 19.1.

3'-O-(t-Butyldimethylsilyloxyamino)carbonyl-5'-O-tert-butyldiphenylsilyl-2,2'-anhydrouridine (15):

5'-O-TBDPS-2,2'-Anhydrouridine (14; 5.0 g, 11 mmol) was co-evaporated with anhydrous pyridine then dissolved in 110 mL of anhydrous pyridine. The flask was flushed with nitrogen, and the 2.3 g (14 mmol) of 1,1'-carbonyldiimidazole was added in one portion as a solid. The solution was stirred at room temperature under nitrogen for 16 hr. A 1 mL aliquot was removed, diluted with 100 mL of ethyl acetate, and washed twice with 100 mL of water. The ethyl acetate layer was dried over sodium sulfate and concentrated in vacuo. $^1$H NMR Analysis indicated complete conversion of starting material. To the reaction mixture was added 2.97 g (19.9 mmol) of O-(t-butyldimethylsilyl) hydroxylamine and the reaction was stirred at room temperature under nitrogen for 5 hr. An additional 0.2 eq (0.32 g) of O-(t-butyl-dimethylsilyl)hydroxylamine was added and the reaction was stirred for 16 hr. The reaction was concentrated in vacuo at <30° C. and the crude residue dissolved in CH$_2$Cl$_2$. The organic phase was washed with NaHCO$_3$ solution, dried over Na$_2$SO$_4$, and concentrated. This material was filtered through 500 mL of silica gel in a sintered glass funnel, eluting with first 1000 mL hexanes, then with 1000 mL of 50% hexane in EtOAc, then with 500 mL EtOAc, then 500 mL MeOH/EtOAc (1:9), and finally with 1000 mL 20% MeOH in EtOAc collecting 500 mL fractions. Concentration of the product containing fractions afforded 5.12 g (73%) of 15 as a glassy foam. 15: $^1$H NMR (300 MHz, d6-DMSO) d 10.46 (br s, NH), 7.93 (d, J=7.5 Hz, H6), 7.55–7.31 (m, 10H), 6.38 (d, J=5.7 Hz, H1'), 5.89 (d, J=7.5 Hz, H5), 5.28 (d, J=5.7 Hz, H2'), 5.40 (d, J=3.2 Hz, H3'), 4.35 (m, H4'), 3.59 (dd, J=11.3, 5.3 Hz, H5'), 3.50 (dd, J=11.3, 6.4 Hz, H5'), 0.91 (s, 9H), 0.13 (s, 3H), 0.12 (s, 3H); Anal. Calc'd for C$_{32}$H$_{43}$N$_3$O$_7$Si$_2$: C, 60.27; H, 6.79; N, 6.59; found: C, 59.16; H, 6.89; N, 6.63.

Base Catalyzed cyclization of 3'-O-(t-Butyldimethylsilyloxyamino)-carbonyl-5'-O-tert-butyldiphenylsilyl-2,2'-anhydrouridine (16, 17, and 18):

To a stirred, 23° C. solution of 3.0 g (4.7 mmol) of 15 in 45 mL of THF was added 70 mL (0.47 mmol) of DBU. After 16 h, TLC analysis showed remaining starting material as well as higher Rf spots. An additional 70 mL of DBU was added and the mixture was stirred 2 h then concentrated in vacuo. Purification of the crude residue by column chromatography (350 mL of SiO$_2$ packed in hexanes, eluting with hexanes, then a gradient of 25–50–75% EtOAc in hexanes, then EtOAc, and finally 10% MeOH in EtOAc) afforded 16 (27%) as the highest Rf product as well as regioisomer 18 (9%) as the intermediate Rf product, and desilylated product 17 (36%) as the low Rf product. Data for 16: mp 94–96° C.; $^1$H NMR (300 MHz, DMSO-d6) d 11.52 (s, 1H), 7.68–7.61 (m, 5H), 7.49–7.41 (m, 6H), 6.11 (d, J=4.56 Hz, 1H), 5.53 (d, J=8.01 Hz, 1H), 5.19 (dd, J=7.80, 3.69 Hz, 1H), 4.69 (dd, J=7.77, 4.56 Hz, 1H), 4.29 (q, J=4.69 Hz, 1H), 3.91–3.86

(m, 2H), 1.01 (s, 9H), 0.85 (s, 9H), 0.138 (s, 3H), 0.01 (s, 3H); $^{13}$C NMR (75 MHz, CDCl$_3$) d 164.3, 158.0, 150.3, 141.9, 136.2, 136.0, 133.5, 133.0, 132.7, 130.9, 130.8, 128.7, 128.6, 103.7, 90.6, 86.1, 76.5, 67.6, 63.6, 27.0, 25.7, 19.3, 17.8, 0.5; Anal. Calc'd for C$_{32}$H$_{43}$N$_3$O$_7$Si$_2$: C, 60.27; H, 6.79; N, 6.59; found: C, 59.11; H, 6.66; N, 6.33.

Data for 17 mp 219–220° C.; $^1$H NMR (300 MHz, DMSO-d6) d 11.53 (s, 1H), 10.25 (s, 1H), 7.65–7.59 (m, 5H), 7.47–7.36 (m, 6H), 5.90 (br s, 1H), 5.52 (d, 7.95H), 5.17 (dd, J=8.07, 5.55 Hz, 1H), 4.69 (br d, 8.8H), 4.19 (q, J=5.3 Hz, 1H), 3.92–3.83 (m, 2H), 0.99 (s, 9H); $^{13}$C NMR (75 MHz, DMSO-d6) d 164.1, 157.1, 151.0, 143.9, 135.9, 135.8, 133.5, 133.2, 130.7, 128.7, 128.6, 102.7, 91.3, 86.5, 79.6, 67.9, 64.0, 26.7, 18.9; Anal. Calc'd for C$_{26}$H$_{29}$N$_3$O$_7$Si: C, 59.64; H, 5.58; N, 8.02; found: C, 59.41; H, 5.61; N, 7.85.

Data for 18

$^1$H NMR (300 MHz, DMSO-d6) d 11.46 (s, 1H), 7.78 (d, J=8.1 Hz, 1H), 7.63–7.59 (m, 4H), 7.47–7.36 (m, 6H), 5.98 (br s, 1H), 5.74 (br d, J=6.72 Hz, 1H), 5.60 (d, J=7.95 Hz, 1H), 5.39 (dd, J=6.60, 4.35 Hz, 1H), 4.27 (q, J=5.3 Hz, 1H), 3.92 (dd, J=10.9, 5.1 Hz, 1H), 3.83 (dd, J=10.7, 6.8 Hz, 1H), 0.98 (s, 9H), 0.91 (s, 9H), 0.09 (s, 6H); $^{13}$C NMR (75 MHz, CDCl$_3$) d 164.2, 160.4, 150.7, 143.5, 136.3, 136.1, 133.5, 133.2, 130.7, 128.5, 128.4, 103.6, 94.6, 87.1, 86.5, 81.8, 63.8, 26.8, 26.3, 19.2, 18.4, −5.5; Anal. Calc'd for C$_{32}$H$_{43}$N$_3$O$_7$Si$_2$: C, 60.27; H, 6.79; N, 6.59; found: C, 59.39; H, 6.93; N, 6.28.

EXAMPLE 3

Preparation of a 2'-hydroxylaminouridine derivative by catalytic base-promoted cyclofunctionalization, conversion of the nucleoside to the nucleotide triphosphate, and enzymatic modified oligonucleotide synthesis.

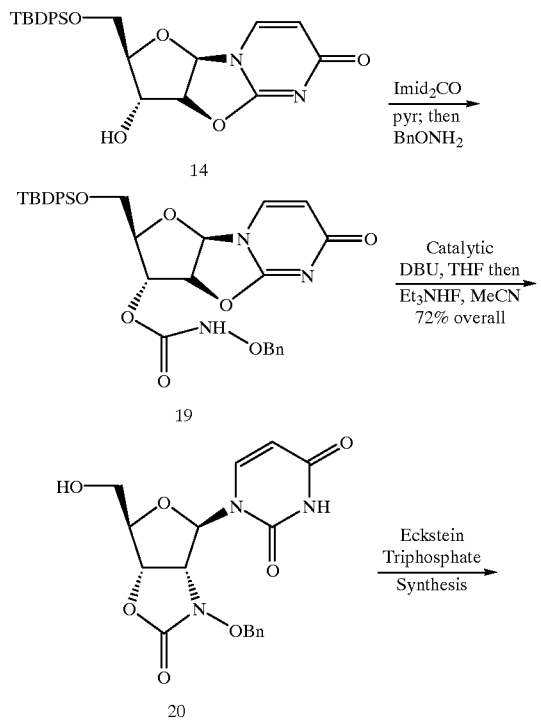

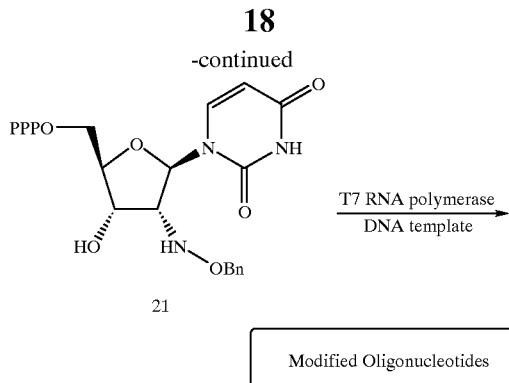

A cyclofunctionalization protocol for the introduction of 2'-NHOR functionality has been developed in which a catalytic amount of base is employed. This scheme has proven suitable for the preparation of the nucleotide triphosphate analog of 2'-deoxy-2'-benzyloxyaminouridine. In the event, 5'-TBDPS anhydrouridine 14 (for preparation, see Example 2) is functionalized by sequential treatment with carbonyldiimidazole and BnONH$_2$ in pyridine. The cyclization precursor 19 thus prepared is isolated in 93% yield after silica gel filtration. Cyclization is facilitated by treatment of an anhydrous THF solution of the precursor with 10 mole percent of DBU for 24 hours, followed by desilylation of the 5'-OH (TEAHF, MeCN) affords the benzyloxyamine nucleoside analog 21 in 72% overall yield which is suitably derivatized for conversion to the triphosphate. By following a procedure similar to that reported by Ludwig and Eckstein, the corresponding, novel nucleotide triphosphate has been prepared. We found a slight modification of the reported procedure to be preferable in which stoichiometric amounts of the chlorophosphorinone reagent (as reported) and the pyrophosphate solution (vs. 1.5 equivalents of the pyrophosphate utilized by Eckstein) were employed. Furthermore, we found NaIO$_4$ solution, rather than the reported I$_2$/water/pyridine system, to be a superior oxidant. NH$_4$OH solution treatment was carried out to cleave the 2'-N,3'-O carbonyl of the substrates. We have found the crude triphosphates prepared in this manner to be of suitable purity for use in transcription reactions without further purification by Sephadex. This 2'-modified triphosphate may have interesting applications in the SELEX protocol itself, as well as, in principle, serve as a precursor to the known 2'-NH$_2$-2'-deoxy UTP and/or the novel 2'-NHOH-2'-deoxy UTP.

2'-Amino and 2'-fluoro pyrimidine triphosphates have been shown to serve as suitable substrates for modified oligo synthesis via DNA template-directed synthesis with T7 RNA polymerase (Aurup, H.; Williams, D. M.; Eckstein, F. Biochemistry, 1992, 31, 9636. For applications of 2'-NH$_2$ and 2'-F NTPs in SELEX, see U.S. patent application Ser. No. 08/117,991, filed Sep. 8, 1992 and entitled "High Affinity Nucleic Acid Ligands containing Modified Nucleotides"). We have now expanded the scope of 2'-modifications to include the 2'-deoxy-2'-benzyloxyamino UTP derivative. 2'-Benzyloxy amino UTP (21) has been incorporated into modified oligonucleotides via DNA template directed synthesis with T7 RNA polymerase. While preliminary transcription studies (employing standard in house assays for transcriptions of random as well as a fixed sequence DNA templates) revealed the efficiency of the benzyl derivative to be 6.8% that of 2'-NH$_2$ UTP at equal concentrations (1 mM), doubling the concentration of benzyloxyamino UTP to 2 mM improved the relative efficiency to 13.3% of that of the amino analog (at 1 mM). The effect of 2'-NHOBn UTP concentration vs. effeciency of incorporation was evaluated and a maximum efficiency of incorporation of approximately 19% of that of 1 mM 2'-amino uridine triphosphate incorporation was observed at an analog concentration of 4 to 5 mM. These data are encouraging for the prospective optimization of the transcription conditions for this particular triphosphate, as well as for the potential SELEX compatibilty of this and other proprietary 2'-deoxy-2'-NHOR (including the parent derivative where R=H) nucleotide triphosphate derivatives.

General Experimental Information

Anhydrous dioxane and anhydrous pyridine from Aldrich Sure-Seal bottles were used and were sparged with Ar prior to setting up reaction. 0.5 Molar $(Bu_3NH^+)_2H_2P_2O_7^{2-}$ solution in DMF was prepared according to the reported procedure (Ludwig, J.; Eckstein, F. *J. Org. Chem.* 1989, 54, 631) and was sparged with Ar prior to setting up reaction. $^{31}P$ NMR Spectra were measured on samples prepared by dissolving ca 100 mL aliquots of the reaction mixture in ca 600 mL of $CD_3CN$ or $D_2O$. The 5'-OH-nucleoside starting material was coevaporated with pyridine 2 times in the oven-dried reaction flask directly prior to setting up the reaction. A new bottle of 2-chloro-4H-1,3,2-benzodioxaphosphorin-4-one was sublimed at 50° C., transferred to small vials in a glove bag, and stored in a dessicator at 0° C. In this manner, the reagent may be dissolved in sparged, anhydrous solvent and transferred via syringe. Acceptable purity of the chlorophosphorinone and pyrophosphate solution was confirmed by $^{31}P$ NMR analysis directly prior to setting up the triphosphate reaction.

3'-O-(Benzyloxyamino)carbonyl-5'-O-tert-butyldiphenylsilyl-2,2'-anhydrouridine (19):

To a stirred, 23° C. solution of 10.0 g (21.5 mmol) of 14 in 40 mL of pyridine was added 3.67 g (22.6 mmol; 1.05 equiv) of 1,1'-carbonyldiimidazole. The mixture was stirred until conversion to the corresponding carbonylimidazole was complete [as determined by $^1H$ NMR analysis of concentrated aliquots; ca.12 h: Signals characteristic of the acyl imidazole intermediate: $^1H$ NMR (300 MHz, $CDCl_3$) d 6.30 (d, J=5.7 Hz, H1'), 5.98 (d, J=7.5 Hz, H5), 5.73 (br d, J=2.1 Hz, H3'), 5.55 (br d, J=5.7 Hz, H2'), 4.51 (m, J=6.5, 2.2 Hz, H4'), 3.68 (dd, J=11.3, 6.0 Hz, H5'), 3.56 (dd, J=11.3, 7.1 Hz, H5'), 1.00 (s, 9H).], at which time 2.9 g (3.72 mmol) of O-benzylhydroxyamine was added. The mixture was stirred 3 h, concentrated in vacuo, and purified by filtration through 1000 mL of silica gel in a sintered glass funnel (eluting with EtOAc (1 L) then 5% then 7.5% MeOH in EtOAc (1 L each), then 10% and 15% MeOH in EtOAc (2 L each); 800–1000 mL fractions) afforded 12 g (93%) of the product as a white chalk. Data for 19: mp 107.2–108.8° C.; $^1H$ NMR (300 MHz, $CDCl_3$) d 7.81 (br s, NH), 7.55 (m, 4H), 7.41–7.25 (m, 11H), 7.26 (s, 1H), 7.25 (d, J=7.6 Hz, H6), 6.12 (d, J=5.7 Hz, H1'), 5.93 (d, J=7.5 Hz, H5), 5.43 (br d, J=2.0 Hz, H3'), 5.29 (br d, J=5.6 Hz, H2'), 4.88 (s, 2H, $OCH_2Ph$), 4.32 (dt, J=6.3, 2.1 Hz, H4'), 3.51 (dd, J=11.3, 6.3 Hz, H5'), 3.50 (dd, J=11.2, 6.4 Hz, H5'), 1.01 (s, 9H). Anal. Calcd for $C_{33}H_{35}O_7N_3Si$ C, 64.58; H, 5.75; N, 6.85. Found C, 63.94; H, 5.81; N, 6.85.

DBU Catalyzed cyclization of 3'-O-(Benzyloxyamino)carbonyl-5'-O-tert-butyldiphenylsilyl-2,2'-anhydrouridine:2'-Benzyloxyamino-5'-O-tert-butyldiphenylsilyl-2'-N,3'-O-carbonyl-2'-deoxyuridine:

To a stirred, 23° C. solution of 8 g (13.03 mmol) of 19 in 110 mL of THF (0.12 M) was added 0.2 mL (0.13 mmol) of DBU. After 48 h, the mixture was concentrated in vacuo and the crude residue dissolved in EtOAc. The organic solution was washed once with saturated $NaHCO_3$ solution, dried over $Na_2SO_4$, filtered, and concentrated. No further purification of the product was carried out. An analytical sample was purified by silica gel chromatography (eluting with hexanes/EtOAc) $^1H$ NMR (300 MHz, $CDCl_3$) d 8.22 (br s, NH), 7.68–7.56 (m, 4H), 7.49–7.32 (m, 11H), 6.78 (d, J=8.1 Hz, H6), 5.43 (dd, J=8.1, 1.9 Hz, H5 [w/$D_2O$ this signal was observed as a doublet, J=8.1]), 5.16 (d, J=2.1 Hz, H1'), 5.09 (dd, J=8.1, 5.0 Hz, H3'), 5.08 (d, J=11.6 Hz, $OCH_2Ph$), 5.02 (d, J=11.6 Hz, 1H, $OCH_2Ph$), 4.23 (dd, J=8.1, 2.1 Hz, H2'), 4.18 (q, J=4.7 Hz, H4'), 3.91 (dd, J=11.3, 4.2 Hz, H5'), 3.81 (dd, J=11.4, 4.5 Hz, H5'), 1.02 (s, 9H); $^{13}C$ NMR (75 MHz, $CDCl_3$) d 164.44, 158.07, 150.40, 142.65, 136.47, 136.28, 136.09, 133.43, 133.04, 130.79, 130.03, 129.68, 128.57, 103.24, 92.09, 86.61, 78.69, 76.43, 67.69, 63.52, 26.89, 19.25.Anal. Calcd for $C_{33}H_{35}O_7N_3Si$ C, 64.58; H, 5.75; N, 6.85. Found C, 64.78; H, 5.88; N, 7.18.

2'-Benzyloxyamino-2',3'-N,O-carbonyl-2'-deoxyuridine (20):

The crude 2'-benzyloxyamino-5'-O-tert-butyldiphenylsilyl-2'-N,3'-O-carbonyl-2'-deoxyuridine (13.03 mmol) prepared above was dissolved in 50 mL of MeCN and treated with 1.89 g (15.6 mmol) of solid $Et_3NHF$. The mixture was stirred 48 h, at which time no starting material remained by TLC analysis. The reaction mixture was concentrated to ¼ the original volume and then applied directly to a column of 400 mL of silica gel packed in EtOAc. The product was eluted with EtOAc to afford 3.5 g (72% overall from 19). Data for compound 20: $^1H$ NMR (300 MHz, $CDCl_3$) d 11.49 (s, 1H), 7.67 (d, J=8.1 Hz, 1H), 7.42–7.36 (m, 5H), 5.96 (d, J=2.2 Hz, 1H), 5.68 (dd, J=8.0, 1.5 Hz, 1H), 5.19 (t, J=5.4 Hz, 1H), 5.07–4.99 (m, 3H), 4.68 (dd, J=8.2, 2.2 Hz, 1H), 4.11 (q, J=4.8 Hz, 1H), 3.63 (t, J=5.1 Hz, 2H.

2'-Benzyloxyamino-2'-deoxyuridine 5'-O-triphosphate (21):

To a stirred solution of 0.61 g (1.64 mmol) of the nucleoside 20 in 6 mL of pyridine under Argon was added a solution of 0.35 g (1.72 mmol, 1.05 equiv) of 2-chloro-4H-1,3,2-benzodioxaphosphorin-4-one in 6 mL of dioxane. After 60 min, $^{31}P$ NMR analysis showed clean conversion to the 5'-nucleoside phosphorinone ($^{31}P$ NMR, (121.5 MHz, $CD_3CN$ d 131.54, 131.47). To this solution was added 0.39 mL of $Bu_3N$ via syringe followed immediately by addition of 3.25 mL (1.64 mmol, 1 equiv) of the pyrophosphate solution. After 60 min, $^{31}P$ NMR analysis showed clean conversion to the anticipated cyclic intermediate ($^{31}P$ NMR, $CD_3CN$ d 113.21 (t, J=43 Hz), −13.51 (d, J=43 Hz)). At this stage, several different oxidation conditions were evaluated by treating 2 mL aliquots of the reaction mixture with different oxidation conditions. The cyclic intermediate seems to be relatively stable if stored at 0° C., although impurity peaks in the $^{31}P$ NMR were observed to increase in intensity over 48 h. Oxidation systems studied thus far include the standard $I_2$/pyridine/water system, 70% tBuOOH/water, solid $NaIO_4$, and 0.1 M $NaIO_4$ solution. The best results (2 separate experiments) to date, as determined by $^{31}P$ NMR analysis of the crude oxidation reactions, were obtained by employing an aqueous, 0.1 M $NaIO_4$ solution. Treatment of the reaction mixture with 1 equivalent of 0.1 M $NaIO_4$ solution, followed after 30 seconds with excess solid $Na_2SO_3$ resulted clean transformation to the linear triphosphate intermediate [$^{31}$P NMR (121.5 MHz, D$_2$O) d −2.5 (br d), −4.0 (d, J=18 Hz), −14.6 (br t)]. It is noteworthy that chemical shifts and peak resolution observed in $^{31}$P NMR spectra of this intermediate, and other triphosphates, varied somewhat from sample to sample, presumably as a result of crude material salt forms or sample concentration, etc . . . . The reaction mixture was concentrated in vacuo at <30° C., diluted with water, and washed with CH$_2$Cl$_2$ until the organic phase was colorless. The water layer was concentrated in vacuo at <30° C. to afford a white foam. Examination of the crude material by $^{31}$P and $^1$H NMR analysis showed remarkably clean 2',3'-protected triphosphate. Treatment of this triphosphate with concentrated NH$_4$OH for one hour resulted in conversion to the final product 21. $^1$H NMR (300 MHz, D$_2$O) d 7.81 (d, J=8.1, H6), 7.40–7.29 (m, 5H), 6.15 (d, 7.5 Hz, H1'), 5.89 (d, J=8.1, H5), 4.69 (s, 2H, PhCH$_2$), 4.61 (m, 1H), 4.27–4.20 (m, 3H), 3.86 (t, J=7.1), 3.20 (q, J=7.3, Et$_3$NH$^+$), 1.27 (t, J=7.3, Et$_3$NH$^+$): $^{31}$P NMR (121.5 MHz, D$_2$O) d −1.3 (d, J=19 Hz), −6.5 (d, J=19 Hz), −17.04 (t, J=19 Hz). Also observed was a broadsignal at d −1.98.

EXAMPLE 4

Intramolecular introduction of 2'-alkyl substituents.

The cyclofunctionalization of the 2'-position of 2,2'-anhydrouridine can also be exploited for the introduction of carbon substituents. This is a particular attractive feature of the present invention. No general technology exists in the literature for preparation of 2'-alkyl substituted nucleosides. Cleavage of the initial 2',3'-cyclic intermediates generates functionalized 2'-alkyl substituents which can be derivatized further.

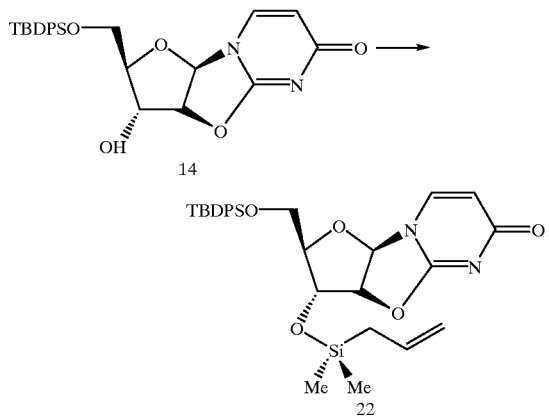

5'-O-tert-Butyldiphenylsilyl-3'-O-(allyldimethyl)silyl-2,2'-anhydrouridine (22):

To a stirred, 0° C. solution of 0.5 g (1.08 mmol) of 5'-O-tert-butyldiphenylsilyl-2,2'-anhydrouridine in 4 mL Et$_3$N/CH$_2$Cl$_2$ (1:3) was added 173 mL (1.18 mmol) of allyldimethylsilyl chloride. The mixture was allowed to warm to ambient temperature and stirred 16 h. The mixture was concentrated in vacuo and applied directly to a column of 75 mL silca gel, eluting with EtOAc then MeOH in EtOAc (1:19 then 1:9 then 1.5:8.5) to afford 200 mg (40%) of recovered starting nucleoside 330 mg (54%) of the higher Rf product 22. $^1$H NMR (300 MHz, CDCl$_3$) Δ 7.61–7.57 (m, 4H), 7.46–7.29 (m, 6H), 7.27 (d, H6), 6.14 (d, J=5.8 Hz, H1'), 5.99 (d, J=7.5 Hz, H5), 5.84–5.71 (m, vinyl H), 5.16 (dd, J=5.7, 1.0 Hz, H2'), 4.96 (br d,vinyl H), 4.92 (br d, vinyl H), 4.70 (br m, H3'), 4.20–4.13 (m, H4'), 3.51 (dd, J=11.2, 5.3 Hz, H5'), 3.49 (dd, J=11.2, 6.9 Hz, H5'), 0.96 (s, 9H), 0.01 (s, 6H).

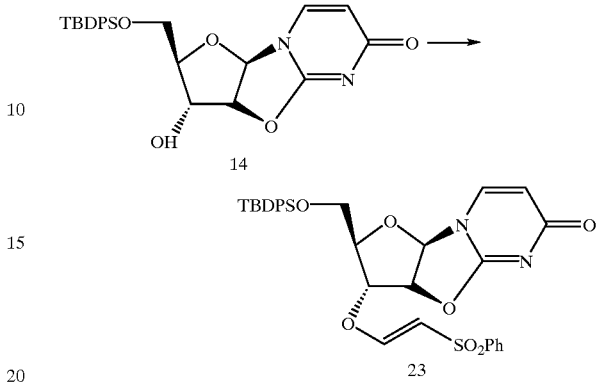

5'-O-tert-Butyldiphenylsilyl-3'-O-[(E)-2-(phenylsulfonyl)-ethenyl]-2,2'-anhydrouridine (23):

To a stirred, 0° C. slurry of 3.0 g (6.46 mmol) of 5'-O-tert-butyldiphenylsilyl-2,2'-anhydrouridine and 2.39 g of trans-1,2-bis(phenylsulfonyl)ethylene (7.76 mmol) in 30 mL of anhydrous THF was added 196 mg (7.76 mmol) of 95% NaH. The mixture was stirred under argon and allowed to warm to ambient temperature.

After 24 h, the mixture was diluted with 300 mL CH$_2$Cl$_2$ and the organic solution washed with NaHCO$_3$ solution, dried over Na$_2$SO$_4$ and concentrated in vacuo. Chromatography of the crude residue on 200 mL of silica gel eluting with EtOAc then MeOH in EtOAc (1:19 then 7.5:92.5 then 1:9) afforded 3.8 g (93%) of the product as a pale yellow foam. $^1$HNMR (300 MHz, CDCl$_3$) Δ 7.80 (d, 2H), 7.78–7.35 (m, H11) 7.25 (d, J=7.5 Hz, H6), 6.29 (d, J=5.8 Hz, H1'), 6.05 (d, J=12.4 Hz, vinyl H), 5.91 (d, J=7.5 Hz, H5), 5.46 (d, J=5.8 Hz, H2'), 4.89 (br s, H3'), 4.42 (m, H4'), 3.58 (dd, J=11.0, 5.5 Hz, H5'), 3.35 (dd, J=11.0, 8.5 Hz, H5'), 0.97 (s, 9H); $^{13}$C NMR (75 MHz, CDCl$_3$) Δ 172.1, 159.9, 158.3, 142.3, 136.1, 136.0, 135.3, 134.0, 132.9, 132.5, 131.0, 130.1, 130.9, 128.8, 128.7, 127.8, 111.1, 110.9, 90.7, 86.2, 85.2, 83.3, 62.5, 26.8, 19.1.

EXAMPLE 5

Stereospecific reduction of the 2'-position.

The technology for intramolecular introduction of a substituent to the 2'-position of 2,2'-anhydrouridine via an activatable 3'-substituent can also be exploited for stereospecific reduction of the 2'-position. The conversion of the 2,2'-anhydrouridine to 2'-deoxyuridine (reported below) may not be of commercial utility. However, instead of a hydride, a deuterium or tritium label can be introduced to the 2'-position in analogous fashion to give stereospecifically labeled pyrimidine nucleosides.

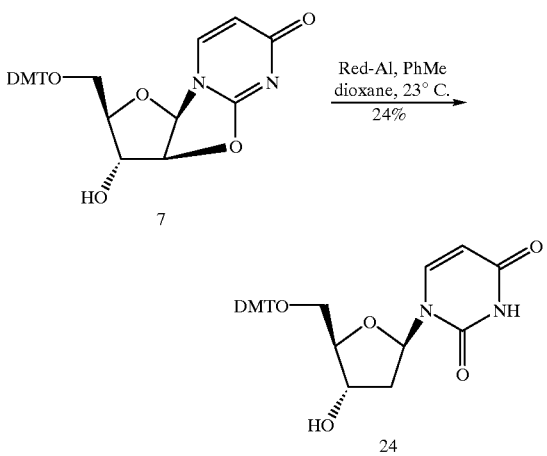

5'-O-Dimethoxytrityl-2'-Deoxyuridine (24).

A solution of 5'-dimethoxytrityl anhydrouridine 7 (200 mg, 0.38 mmoles) in dioxane (3 mL) and toluene (9 mL) was added RED.AL (sodium bis(2-methoxyethoxy)aluminum hydride, 136 μl of a 3.4 M solution in toluene) and the reaction was stirred 16 h at room temperature. The reaction was quenched by addition of sodium chloride solution and the phases partitioned, the organic phase washed with sat. ammonium chloride, dried with magnesium sulfate and evaporated. The residue was purified on silica gel eluting with 5–10% methanol/dichloromethane to afford 24 as an oil (50 mg). NMR (DMSO-$d_6$) Δ 2.19 (t, 2 H, H2', J=2 Hz), 3.19 and 3.21 (ABX, 2 H, H5',5"), 3.72 (s, 6 H, OCH$_3$), 3.87 (m, 1 H, H4') 4.29 (m, 1 H, H3'), 5.37 (br d, 2 H, H5, OH), 6.75 and 6.9 and 7.12–7.4 (m, 13 H, DMT), 7.64 (d, 1 H, H6), 11.36 (br s, 1 H, NH)

EXAMPLE 6

5-Bromo-2,2'-anhydrouridine; Preparation and 2'-Derivitization via Intramolecular Nucleophilic Anhydro Ring Openings.

The scope of the general synthetic method for intramolecular nucleophilic opening of anhydrouridine expands to include a 5-substituted anhydrouridine derivative. 5-Bromo-2,2'-anhydrouridine (26) was prepared in 79% yield from 5'-bromouridine 25 upon treatment with diphenylcarbonate and NaHCO$_3$ in DMF at 80° C. 5'-O-TBDPS derivitization was accomplished affording cyclization precursor 27. This substrate was subjected to a modified version of tricholoracetimidate cyclization described in Example 1 (CCl$_3$CN, 1 equiv Cs$_2$CO$_3$; 23° C.; 97%) to afford high yields of the desired tricholoromethyl oxazoline 28. Acid promoted hydrolysis of the oxazoline ring provided the 2'-NH$_2$ derivative 29.

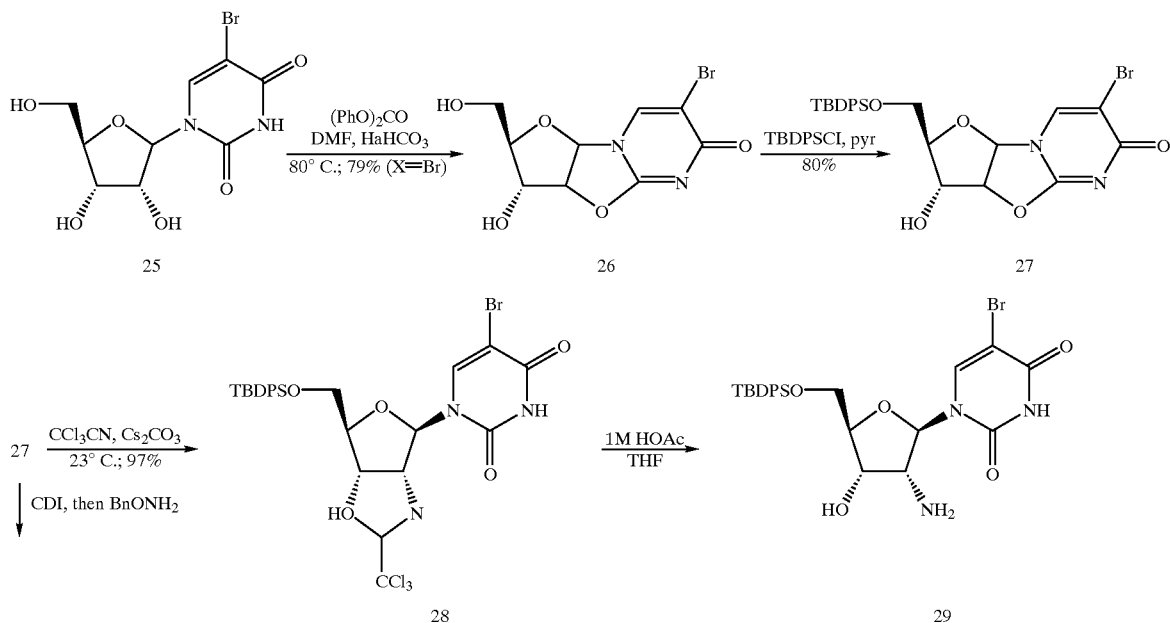

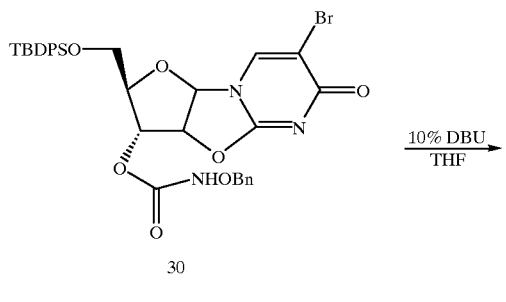
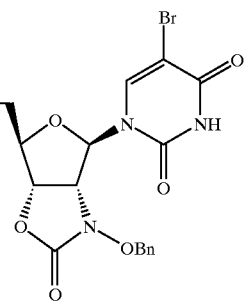

Conversion of 27 to the corresponding 3'-O-carbonylimidazole, followed by benzyloxyamine conjugation afforded cyclization precursor 30, which, upon treatment with 10 mol % DBU in THF resulted in anhydro ring-opened product 31. Products formed by the above processes will be useful for constructing 5-position modified nucleosides that are also modified at the 2'-position. Such nucleoside monomers may be useful precursors to functionally modified oligonucleotides by either enzymatic synthesis (via conversion to the nucleoside triphosphate analogues) or automated synthesis (via conversion to phosphoramidites). Furthermore, the derived oligonucleotides should be stabilized toward nuclease degradation, due to the replacement of the mechanistically significant 2'-hydroxyl by $NH_2$, NHOMe, or other non-participating 2'-substituents.

5-Bromo-2,2'-anhydrouridine (26):

A solution of 1.0 g (3 mmol) of 5-bromouridine (25) in DMF was treated with 0.73 g (3.4 mmol) of diphenylcarbonate and the mixture was heated to 80° C. After 5 minutes, 25 mg (0.28 mmol) of $NaHCO_3$ was added. After 2 h, TLC indicated complete conversion of 25 and the reaction mixture was cooled to ambient temperature and concentrated in vacuo to afford a tan oil. This residue was dissolved in methanol and the solution refluxed for 2–3 h. The crude residue was adsorbed on silica gel and purified by flashing through a column of silica gel eluting with MeOH/dichloromethane (2:8). Concentration of the product containing fractions gave 0.65 g (71%) of the anhydronucleoside as a white foam. $^1$H NMR (400 MHz, DMSO-d6) Δ 8.48 (s, 1H, H6), 6.31 (d, J=5.84 Hz, 1H, H1'), 5.89 (d, J=4.40 Hz, 1H), 5.23 (d, J=5.84 Hz, 1H, H2'), 5.00 (t, J=5.12 Hz, 1H), 4.40 (d, J=4.04 Hz, 1H), 4.13–4.11 (m, 1H), 3.31–3.27 (m, 2H), 3.18 (d, J=5.12 Hz, 1H); $^{13}$C NMR (100 MHz, DMSO-d6) Δ 166.42, 160.03, 137.42, 106.34, 91.08, 90.45, 90.25, 75.47, 61.42; Low resolution MS m/e calc'd for $C_9H_9BrN_2O$ (M+): 304.0004, found 304.8.

5-Bromo-5'-O-tert-butyldiphenylsilyl-2,2'-anhydrouridine (27):

To a stirred solution of 7.0 g (23 mmol) of 26 in 20 mL of pyridine was added 6.6 mL (25.3 mmol) of TBDPSCl. The mixture was stirred at ambient temperature overnight, then concentrated in vacuo. The crude oil residue was dissolved in $CH_2Cl_2$ and washed with 0.5 N HCl solution (twice), water, and brine. The crude residue was combined with another batch prepared in the same manner from 6.8 g (22.3 mmol) of 26 and 6.4 mL (24.5 mmol) of TBDPSCl, adsorbed on silica gel and purified by flashing through a column of silica gel eluting with hexanes/EtOAc (8:2) then EtOAc. Concentration of the product containing fractions gave 9.93 g (40%) of 27 as a white foam. $^1$H NMR (400 MHz, DMSO-d6) Δ 8.59 (s, 1H), 7.54–7.40 (m, 10H), 6.33 (d, J=4.38 Hz, 1H), 6.04 (d, J=4.38 Hz, 1H), 5.31 (d, J=4.11 Hz, 1H), 4.44 (br Δ, 1H), 4.21 (m, 1H), 3.63 (dd, J=11.72, 4.4 Hz, 1H), 3.46 (dd, J=11.36, 6.60 Hz, 1H), 0.92 (s, 9H); $^{13}$C NMR (100 MHz, DMSO-d6) d 166.16, 159.51, 137.41, 135.50, 135.44, 133.05, 132.92, 130.50, 128.50, 106.75, 90.37, 90.08, 88.00, 74.46, 63.23, 26.95, 19.31; Low resolution MS m/e calc'd for $C_{31}H_{43}BrSiO_5N_3$ (M+Et$_3$NH$^+$): 644.255, found 644.1. Analysis calc'd for $C_{25}H_{27}BrN_2O_5Si$: C, 55.25; H, 5.00; N, 5.16; found: C, 55.02; H, 5.10; N, 5.11. $CCl_3CN$ Cyclization of 27 to afford 28

A suspension of 0.27 g (0.5 mmol) of 27 in 2 mL of $CCl_3CN$ was treated with 0.16 g (0.5 mmol) of $Cs_2CO_3$. The mixture was stirred at ambient temperature for 4 h during which time it turned brown, then was concentrated in vacuo. The crude residue was filtered through a pad of silica gel to afford 0.33 g (97%) of 28 as a tan solid. $^1$H NMR (400 MHz, DMSO-d6) Δ 10.05 (s, 1H), 8.62 (s, 1H), 7.53–7.40 (m, 10H), 6.44 (d, J=5.96 Hz, 1H), 5.63 (d, J=2.56 Hz, 1H), 5.59 (d, J=5.96 Hz, 1H), 4.51 (m, 1H), 3.72 (dd, J=11.92, 4.68 Hz, 1H), 3.54 (m, 1H), 0.93 (s, 9H); Low resolution MS m/e calc'd for $C_{33}H_{43}BrCl_3O_5N_4Si$ (M+Et$_3$NH$^+$): 788.1671, found 788.9. Analysis calc'd for C27H27BrCl3N3O5Si: C, 47.14; H, 3.96; N, 6.11; found: C, 46.88; H, 4.02; N, 6.11.

2'-Amino-5-bromo-5'-O-tert-butyldiphenylsilyl-2'-deoxyuridine (29):

To a stirred solutiom of 200 mg (0.3 mmol) of 28 in 0.5 mL of THF was added 1 mL of 50% HOAc. After 4 h, the mixture was neutralized by addition of saturated $NaHCO_3$ solution and the aqueous phase extracted with $CH_2Cl_2$. The organic phase was dried over $Na_2SO_4$ and concentrated. The crude residue was purified by flash silica gel column chromatography (eluting with 6% then 10% MeOH in $CH_2Cl_2$) to afford 100 mg (60%) of 29 as a pale yellow solid. $^1$H NMR (400 MHz, DMSO-d6) Δ 8.59 (s, 1H), 7.56–7.36 (m, 10H), 6.32 (d, J=5.52 Hz, 1H), 6.03 (d, J=4.28 Hz, 1H), 5.30 (dd, J=5.08, 1.47 Hz, 1H), 4.45 (br m, 1H), 4.20 (m, 1H), 3.62 (dd, J=11.5, 4.2 Hz, 1H), 3.44 (dd, J=11.08, 3.84 Hz, 1H), 0.91 (s, 9H).

5-Bromo-3'-O-benzyloxylaminocarbonyl-5'-O-tert-butyldiphenylsilyl-2,2'-anhydrouridine (30):

To a stirred solution of 0.28 g (0.5 mmol) of 27 in 2 mL of pyridine was added 0.09 g (0.53 mmol) of CDI. The mixture was stirred overnight, then 0.07 g (0.55 mmol) of $BnONH_2$ was added. After 3 days, the mixture was concentrated in vacuo and the residue dissolved in $CH_2Cl_2$. The organic phase was washed with saturated sodium bicarbonate solution, water, and brine, then concentrated in vacuo. The crude residue was adsorbed on silica gel and purified by flashing through a column of silica gel eluting with EtOAc. Concentration of the product containing fractions gave 0.165 g (51%) of 30 as a white foam. $^1$H NMR (400 MHz, DMSO-d6) Δ 10.89 (br s, 1H), 8.61 (s, 1H), 7.55–7.39 (m, 15H), 6.39 (d, J=5.56 Hz, 1H), 5.55 (d, J=5.96 Hz, 1H), 5.39 (d, J=2.96 Hz, 1H), 4.81 (s, 2H), 4.39 (m, 1H), 3.66 (dd, J=11.92, 4.48 Hz, 1H), 3.48 (dd, J=11.48, 6.40 Hz, 1H), 0.92 (s, 9H); $^{13}$C NMR (100 MHz, DMSO-d6) Δ 136.2, 135.5, 132.9, 130.6, 130.5, 129.5, 128.9, 128.5, 106.5, 90.1, 87.8, 85.7, 76.6, 63.0, 26.9, 19.3.

5-Bromo-2'-benzyloxylamino-2'-N,-3'-O-carbonyl-5'-O-tert-butyldiphenylsilyl-2'deoxyuridine (31):

To a stirred solution of 160 mg (0.229 mmol) of 30 in 3 mL of THF was added 1 drop of DBU (ca 10 mol %). The mixture was stirred overnight, concentrated in vacuo and the crude residue purified on flash silica gel (eluting with 1:1 hexanes-EtOAc) to afford 66 mg (42%) of 31 as a white foam.

EXAMPLE 7

Intramolecular nucleophilic substitution of the 2'-position of purine nucleosides.

The methodology described for anhydropyrimidine opening is applied to the synthesis of modified purine nucleosides as well. One embodiment would involve nucleophilic opening of a suitably derivatized 8,2'-thioanhydroguanosine such as 34 (a known compound described in Ogilvie et al. (1972) Can. J. Chem. 1100). As shown in the scheme below, any of the examples applied to the anhydropyrimidines above may be employed with such guanosine derivatives.

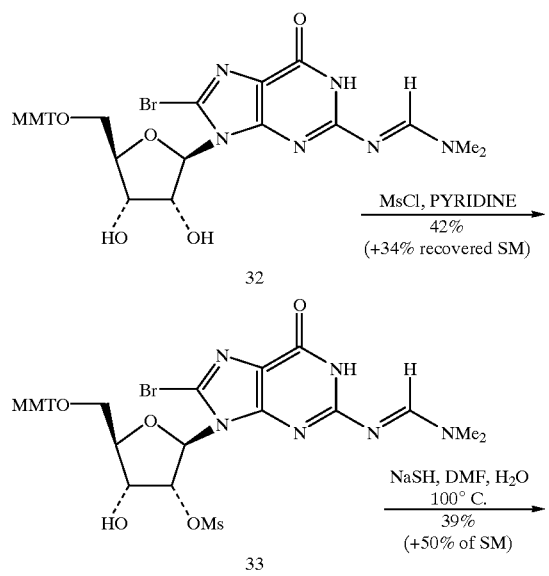

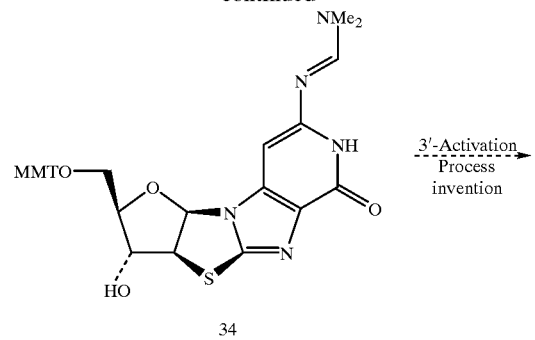

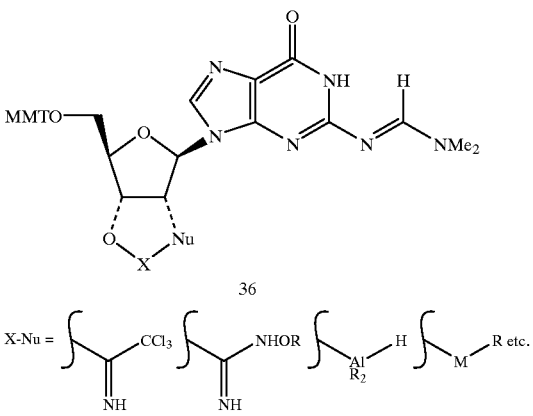

EXAMPLE 8

The preparation of 2'-deoxy-2'-methoxylaminouridine via one-step cyclization/deprotection.

In this example, 3'-methoxyaminocarbonyl-2,2'-anhydrouridine (37) is converted directly into the novel uridine nucleoside 2'-deoxy-2'-methoxyaminouridine (39) via an embodiment of the method of the invention. Additionally, under the reaction conditions, further conversion of the cyclic nucleoside product occurs which results in 2'-N, 3'-O-decarbonylation.

In the event, 5'-TBDPS-2,2'-anhydrouridine (14) is converted to 3'-methoxyaminocarbonyl-2,2'-anhydrouridine 37 via sequential treatment with carbonyldiimidazole and methoxylamine HCl in pyridine (93% yield). Upon treatment of 37 with two equivalents of $Cs_2CO_3$ in methanol, initial cyclization to intermediate 38 takes place, followed by slower conversion to carbonyl deprotected derivative 39 in 68% overall yield from 37.

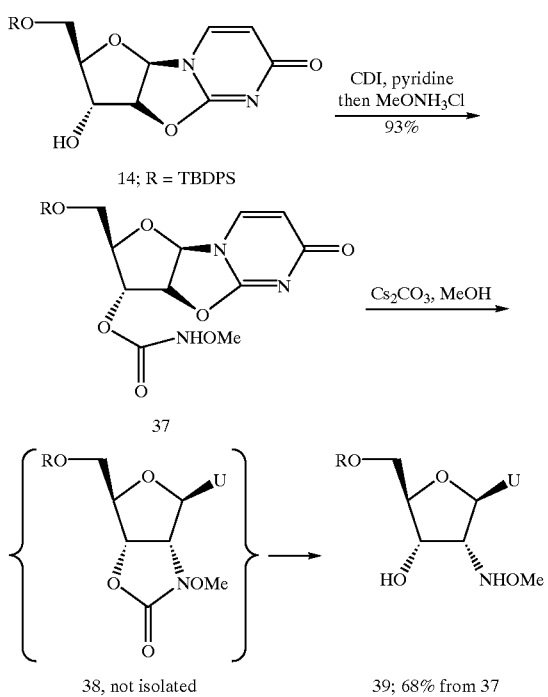

14; R = TBDPS

37

38, not isolated → 39; 68% from 37

5'-O-tert-Butyldiphenylsilyl-3'-O-methoxylaminocarbonyl-2,2'-anhydrouridine (37):

An 0.13 M solution of 5'-O-tert-butyldiphenylsilyl-3'-O-carbonylimidazole-2,2'-anhydrouridine (14; see Example 2) was prepared from 6 g (12.93 mmol) of 5-O-TBDPS 2,2'-anhydrouridine and 2.5 g (15.5 mmol) of carbonyldiimidazole in pyridine. To 14 mL (1.83 mmol) of this solution was added 0.17 g (2.04 mmol; 1.1 equiv) of methoxylamine HCl. The mixture was stirred 3 h, then concentrated in vacuo. The residue was diluted with dichloromethane and washed with satd NaHCO$_3$ solution, dried over Na$_2$SO$_4$, and purified by filtration through flash silica gel chromatography (eluting with EtOAc, then 5%–10%–15%–20% MeOH in EtOAc) to afford 0.89 g (93%) of the product as a white solid. 37: $^1$H NMR (300 MHz, CDCl$_3$) d 8.88 (br s, 1H), 7.57–7.52 (m, 4H), 7.37–7.30 (m, 7H), 6.28 (d, J=5.6 Hz, 1H), 5.89 (d, J=7.4 Hz, 1H), 5.45–5.42 (overlapping signals, 2H), 4.36 (dt, J=5.9, 2.7 Hz, 1H), 3.72 (s, 3H), 3.56 (d, J=5.9 Hz, 2H), 0.98 (s, 9H). $^{13}$C NMR (75 MHz, CDCl$_3$) d 171.7, 159.5,. 155.6, 135.4, 135.1, 132.78, 132.4, 128.0, 127.9, 127.8, 110.0, 90.1, 87.0, 64.6, 62.8, 26.7, 19.1.

5'-O-tert-Butyldiphenylsilyl-2'-deoxy-2'-methoxylaminouridine (39):

To a stirred solution of 0.85 g (1.6 mmol) of 2 in 20 mL MeOH was added 1.05 g (2 equiv) of Cs$_2$CO$_3$. After 20 h, the mixture was concentrated in vacuo and the residue diluted with EtOAc. The organic solution was washed with water and dried over Na$_2$SO$_4$ and concentrated. The residue was purified by chromatography using 100 mL of silica gel (eluting with a solvent gradient ranging from 10% EtOAc hexanes to 100% EtOAc) to afford 0.53 g (68%) of 39 as a white solid. $^1$H NMR (300 MHz, CDCl$_3$) d 7.80 (d, J=8.2 Hz, 1H), 7.65–7.61 (m, 4H), 7.44–7.38 (m, 6H), 6.42 (d, J=5.2 Hz, 1H), 6.01 (d, J=6.7 Hz, 1H), 5.48 (d, J=8.1 Hz, 1H), 4.39 (dd, J=5.5, 2.7 Hz, 1H), 4.15 (br d, J=2.4 Hz, 1H), 3.99 (dd, J=11.8, 2.2 Hz, 1H), 3.83 (dd, J=11.8, 2.4 Hz, 1H), 3.72 (q, J=5.7 Hz, 1H), 3.60 (s, 3H), 1.07 (s, 9H); $^{13}$C NMR (75 MHz, CDCl$_3$) d 163.3, 150.9, 139.8, 135.6, 135.3, 132.6, 132.0, 130.2, 130.1, 128.0, 102.6, 86.8, 85.6, 70.4, 68.1, 64.0, 62.3, 26.9, 19.3.

EXAMPLE 9

Preparation of 3'-ox-2'-azaphospholidine derivatives of nucleosides.

The intramolecular introduction of nucleophiles to the 2'-position of nucleosides also offers an attractive route for preparation of 2'-modified 3'-phosphate- or 3'-phosphite derivatives. Monomers of such kind can have application in synthesis of oligonucleotides with 2'-groups, as well as in synthesis of backbone modified oligonucleotides. Cyclic phosphates, in which the phosphorous bridges the 3'-hydroxyl and the introduced 2'-substituent could also render a novel class of antiviral compounds.

The 5'-protected 2,2'-anhydrouridine reacts with phosphorous oxychloride to give the corresponding 3'-dichlorophosphate derivative. This can be reacted with an equivalent of a nucleophile futher activatable for nucleophilic attack, such as isopropylamine. The latter cyclizes in the presence of a base such as 10% DBU to yield the nucleoside 3'-ox-2'-azaphospholidine derivative. Chloro oxazaphospholidine derivatives of ephedrine are well known stable compounds.[12] Reaction of the latter with an alcohol such as 2-cyanoethanol gives the corresponding 2-cyanoethoxyoxazaphospholidine derivatives.

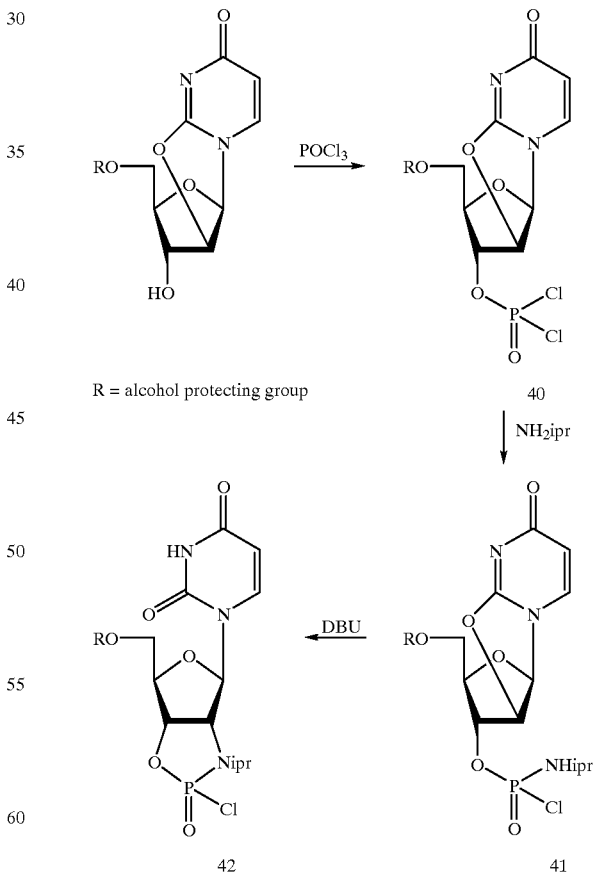

R = alcohol protecting group

40

42    41

EXAMPLE 10

A suspension of 2,2'-O-anhydrouridine (1,10.1 g,0.045 mol) and dimethoxytrityl chloride (17.5 g,1.1 eq) in pyridine (100 ml) and catalytic DMAP (~50 mg) was stirred 16 hrs at rt then evaporated. The residue was washed with dichloromethane/water, the organic phases washed with dilute sodium bicarbonate, dried with magnesium sulfate and evaporated. The resulting foam was purified on silica gel eluting with 0–20% methanol/ethyl acetate to afford the desired material 5'-O-(4,4'-Dimethoxytrityl)-2,2'-anhydro-1-(b-D-arabinofuranosyl)uracil as a foam 13.3 g ,56% yield. 1H NMR (DMSO) d 2.81 and 2.85 (ABX,2,$j_{ab}$=10.2 HZ, $j_{ax}$=4.2 Hz,$j_{bx}$=~1 HZ, H5',5"), 3.73(s,3, OCH3) 4.22(m,1, H3'), 4.31(m,1,H4'), 5.21(d,1,j=5.7 Hz, H2'),5.89(d,1,j=7.4 Hz,H5), 5.96(d,1,j=4.4 Hz,3'-OH)6.33(d,1,j=5.6 Hz,H1'), 6.84,7.16, 7.28(m,13,DMT), 7.96(d,1,j=7.4,H6). Anal. Calcd. for $C_{30}H_{28}N_2O_7$. 0.5$H_2O$: C,67.03; H,5.43; N,5.21. Found: C,67.02; H,5.55 ; N,4.99.

To a solid residue of Magnesium methoxide (0.67 g, 4 equiv., obtained by evaporation of a commercial sample of 10% $Mg(OCH_3)_2$ in methanol to dryness under reduced pressure on a rotary evaporator) in a 100 ml round bottom flask was added 5'-O-(4,4'-Dimethoxytrityl)-2,2'-anhydro-1-(b-D-arabinofuranosyl)uracil (1.0 g, 1.89 mmol) and N,N-dimethylformamide (DMF, 15 ml) and the mixture was heated 4 hrs at 100° C. Thin layer chromatography (TLC) showed the reaction to be complete. Acetone (ml) was added to the reaction mixture and filtered. The filtrate was evaporated to dryness, the residue dissolved in ethyl acetate and washed with water (1×); The solids from the above filtration were dissolved in water and washed with ethyl acetate (2×) and the combined organic phases were dried (MgSO4) and evaporated to afford 5'-O-(4,4,'-Dimethoxytrityl)-2'-O-methyluridine (0.94 g, 88.7% yield, 95% pure by HPLC). 1-H NMR identical to a commercial sample.

EXAMPLE 11

2,2'-O-Anhydrouridine (5.0 g, 22.1 mmol), 4,4'-Dimethoxytrityl Chloride (8.24 g, 24.3 mmol) and N,N-dimethylaminopyridine (DMAP, ~30 mg) was dissolved in pyridine (60 ml) and DMF (20 ml) and the solution stirred 16 hrs at room temperature. The volume was reduced on a rotary evaporator under reduced pressure (bath temperature<40° C.). The residue was diluted with dichloromethane and washed with dil. sodium bicarbonate (2×), the organic phase dried (Magnesium sulfate) and evaporated to an oily residue. The residue so obtained was triturated with ethyl ether (2×). The residue was dissolved in a small amount of dichloromethane and the product precipitated with excess ethyl ether (2×) to afford 10.9 g of crude 5'-O-dimethoxytriyl-2,2'-O-anhydrouridine as a yellow powder. This crude product was combined with 4.2 equivalents of magnesium methoxide (7.56 g); (prepared by evaporation of 90 ml of a 10% $Mg(OCH_3)_2$ solution in methanol to dryness under reduced pressure) in DMF (400 ml) and the reaction heated 16 hrs at 100° C. and then evaporated. Ethyl acetate was added to the residue and the solution was washed with dil. sodium bicarbonate and the aqueous phases back extracted 3× with ethyl acetate, the combined organic phases dried (magnesium sulfate), and the solvent evaporated to afford 5'-O-(4,4'-dimethoxytrityl)-2'-O-methyluridine (12.2 g, 98% yield, >90% pure by 1-H NMR).

EXAMPLE 12

A mixture of 5'-O-dimethoxytrityl-2,2'-O-anhydrouridine (7) (1.0 g, 1.89 mmol), magnesium n-propoxide (1.62 g, 6 equiv.) in DMF (20 ml, anhydrous) was heated 16 hrs then cooled. Ethyl acetate (50 ml) was added and the organic phase washed with dil. sodium bicarbonate, the aqueous phase back extracted twice with ethyl acetate (2×0 the combined organic phases were dried (magnesium sulfate) and evaporated to dryness. The residue was purified by chromatography on silica gel eluting with 20–60% ethyl acetate in hexanes (all containing 1% triethyl amine), the appropriate fractions were pooled and evaporated to afford 5'-O-dimethoxytrityl-2'-O-propyluridine (0.69 g, 62% yield). 1-H NMR d 0.86 (t, 3H, CH3), 1.53 (q, 2H, CH2), 3.25 and 3.3 (ABX, 2H, H-5',5"), 3.53 (dq, 2H, O-CH2), 3.74 (s, 6H, DMT), 3.91 (m, 1H, H-2'), 3.98 (m, 1H, H-4'), 4.17 (m, 1H, H-3'), 5.14 (d, J=6.7 Hz, 1H, 3'-OH), 5.29 (d, J=8.1 Hz, 1H, H-6), 5.81 (d, J=3.6 Hz, 1H, H-1'), 6.91 and 7.24–7.40 (m, 13H, DMT), 7.75 (d, J=8.1 Hz, 1H, H-5), 11.39 (s, 1H, NH).

EXAMPLE 13

Calcium allyl alkoxide used was prepared as follows: Calcium hydride was ground to a powder (7 g) and then refluxed with 300 ml of allyl alcohol for 48 hrs, cooled and filtered and the filtrate evaporated to a sticky solid [Mg(-O-ally)$_2$] which was used as is in the next step. Approx. one half of the above sticky solid was placed in a flask with 5'-O-dimethoxytrityl-2,2'-O-anhydrouridine (1.0 g, 1.29 mmol) and 30 ml anhydrous DMF and the mixture heated 100° C. 16 hrs colled and evaporated. The residue was dissolved in ethyl acetate and washed with dil. sodium bicarbonate, the organic phase dried (MgSO$_4$) and evaporated. The residue was purified by chromatography on silica gel eluting with 50–80% ethyl acetate in hexanes. The appropriate fractions were pooled and evaporated to afford 5'-O-dimethoxytrityl-2'-O-allyluridine (0.42 g, 42% yield). 1-H NMR (300 MHz, DMSO) d 3.24 and 3.28 (ABX, 2H, H-5',5"), 3.74(s, 6H, 2×OCH$_3$), 3.88 (m, 1H, H-2'), 3.97 (m, 2H, allylic CH$_2$), 4.17 (m,1H, H-4'), 4.20 (m, 1H, H-3'), 5.16 and 5.28 (m, 4H, allylic Ha,Hb, H-5, 3'-OH), 5.84 and 5.90 (m, 2H, H-1', allylic Hc), 6.9 and 7.23–7.39 (m, 13H, DMT), 7.73 (d, J=8.1 Hz, 1H, H-6), 11.41 (br s, 1H, NH)

What is claimed is:

1. A method for the synthesis of 2' modified nucleosides which comprises:
   a) performing the intramolecular nucleophilic reaction of an intermediate compound having the formula:

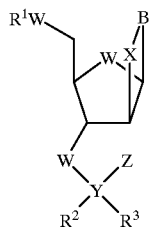

wherein
B is a nucleobase;
W is independently selected from the group consisting of O and S;
X is selected from the group consisting of O, S, NH, and NR$^4$;
Y is selected from the group consisting of a metal, C, Si, Se, S, B, and P;
Z is selected from the group consisting of imidazole, Cl, F, H, $^2$H, $^3$H, OH, NHOR$^1$, NHOR$^5$, NHNHR$^5$, NHR$^5$, =NH, CHCN, CHCl$_2$, SH, SR$^5$, CFH$_2$, CF$_2$H, CR$^2$$_2$Br, OR$^4$;
R$^1$ is selected from the group consisting of H and an alchohol protecting group;

$R^2$ is selected from the group consisting of =O, =S, H, OH, $CCl_3$, $CF_3$, halide, optionally substituted $C_1$–$C_{20}$ alkyl, alkenyl, aryl, $C_1$–$C_{20}$ acyl, benzoyl, $OR^4$ and esters;

$R^3$ is selected from the group consisting of OH, H, $CCl_3$, $CF_3$, halide, $C_1$–$C_{20}$ alkyl, alkenyl, aryl, benzoyl, esters, $OR^4$, omitted as a variable when $R^2$ is =O or =S, and cyclopentadiene, cyclooctadiene, CO, trialkylphosphines if Y is metal;

$R^4$ is selected from the group consisting of an optionally substituted $C_1$–$C_{20}$ alkyl, $C_2$–$C_{20}$ alkenyl, $C_2$–$C_{20}$ alkynyl, and aryl, and phosphate;

$R^5$ is selected from the group consisting of $R^2$, $R^4$, CN, $C(O)NH_2$, $C(S)NH_2$, and $SO_2R^4$, in the presense of a base; and b) isolating said 2' modified nucleoside.

2. The method of claim 1 wherein:

B is selected from the group consisting of a pyrimidine connected to X at the 2-position, a pyrimidine connected to X at the 6-position, and a purine connected to X at the 8-position;

W is O;

X is selected from the group consisting of O, S, and NH;

Y is selected from the group consisting of a metal, C, Si, B, and P;

Z is selected from the group consisting of imidazole, H, $NHOR^1$, $NHOR^5$, $NHNHR^2$, $NHR^2$, =NH, SH, and $OR^4$;

$R^1$ is selected from the group consisting of H and an alcohol protecting group;

$R^2$ is selected from the group consisting of =O, =S, OH, H, $CCl_3$, $CF_3$, halide, $C_1$–$C_{20}$ alkyl, alkenyl, aryl, $C_1$–$C_{20}$ acyl, benzoyl, and ester;

$R^3$ is selected from the group consisting of =O, =S, H, $CCl_3$, $CF_3$, halide, $C_1$–$C_{20}$ alkyl, alkenyl, aryl, benzoyl, esters and omitted as a variable;

$R^4$ is selected from the group consisting of optionally substituted $C_1$–$C_{20}$ alkyl, $C_2$–$C_{20}$ alkenyl, $C_2$–$C_{20}$ alkynyl, and aryl; and $R^5$ is selected from the group consisting of $R^2$ and $R^4$.

3. The method of claim 1 wherein B is a pyrimidine nucleobase.

4. The method of claim 1 wherein B is a purine nucleobase.

5. The method of claim 1 further comprising: c) preparing the 3'-phosphoramidite of said 2' modified nucleoside.

6. The method of claim 1 further comprising: c) preparing the 5'-triphosphate of said 2' modified nucleoside.

7. The method of claim 1 further comprising: c) preparing the 5'-diacylglycerophosphate of said 2' modified nucleoside.

8. A compound prepared according to the method comprising:

a) performing the intramolecular nucleophilic reaction of an intermediate compound having the formula:

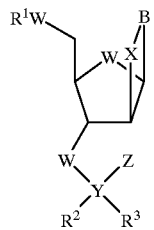

wherein

B is a nucleobase;

W within the ring is S;

W at the 3' and 5' positions of the ring is independently selected from the group consisting of O, S, $CR^2_2$, and $NR^2$;

X is selected from the group consisting of O, S, NH, and $NR^4$;

Y is selected from the group consisting of a metal, C, Si, Se, S, B, and P;

Z is selected from the group consisting of imidazole, Cl, F, H, $^2$H, $^3$H, OH, $NHOR^1$, $NHOR^5$, $NHNHR^5$, $NHR^5$, =NH, CHCN, $CHCl_2$, SH, $SR^5$, $CFH_2$, $CF_2H$, $CR^2_2Br$, $OR^4$;

$R^1$ is selected from the group consisting of H and an alcohol protecting group;

$R^2$ is selected from the group consisting of =O, =S, H, OH, $CCl_3$, $CF_3$, halide, optionally substituted $C_1$–$C_{20}$ alkyl, alkenyl, aryl, $C_1$–$C_{20}$acyl, benzoyl, $OR^4$ and esters;

$R^3$ is selected from the group consisting of OH, H, $CCl_3$, $CF_3$, halide, $C_1$–$C_{20}$ alkyl, alkenyl, aryl, benzoyl, esters, $OR^4$, omitted as a variable when $R^2$ is =O or =S, and cyclopentadiene, cyclooctadiene, CO, trialkylphosphines if Y is metal;

$R^4$ is selected from the group consisting of an optionally substituted $C_1$–$C_{20}$ alkyl, $C_2$–$C_{20}$ alkenyl, $C_2$–$C_{20}$ alkynyl, aryl and phosphate;

$R^5$ is selected from the group consisting of $R^2$, $R^4$, CN, $C(O)NH_2$, $C(S)NH_2$ and $SO_2R^4$ in the presence of a base; and b) isolating said compound.

9. The compound prepared according to the method of claim 8, wherein said method further comprises:

c) preparing the 3'-phosphoramidite of said compound.

10. The compound prepared according to the method of claim 8, wherein said method further comprises:

c) preparing the 5'-triphosphate of said compound.

11. The compound prepared according to the method of claim 8, wherein the method further comprises:

c) preparing the 5'-diacylglycerophosphate of said compound.

12. A method for the synthesis of 2' modified pyrimidines which comprises:

a) performing the intramolecular nucleophilic reaction of an intermediate compound having the formula:

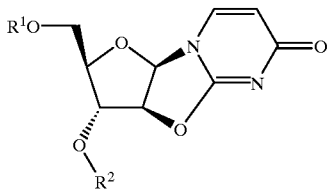

wherein $R^1$ is H or an alcohol protecting group, and $R^2$ is selected from the group consisting of —C(O)NHOTBDMS,

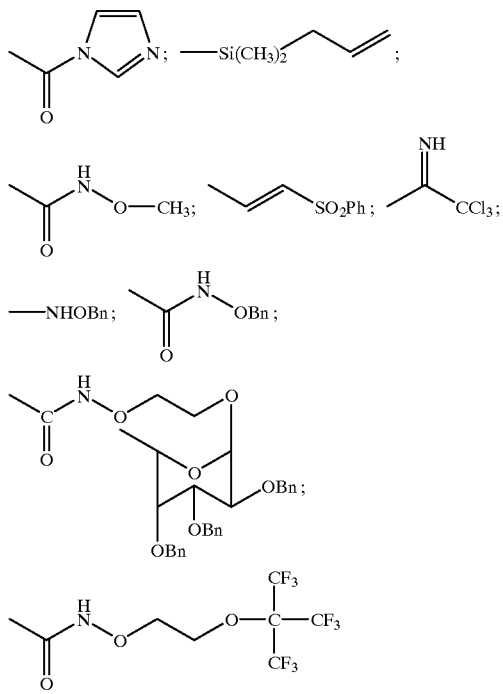

in the presence of a base; and
b) isolating said 2'-modified pyrimidine.

13. The method of claim 12 further comprising:
c) preparing the 3'-phosphoramidite of said 2' modified pyrimidine.

14. The method of claim 13 further comprising:
c) preparing the 5'-triphosphate of said 2' modified pyrimidine.

15. The method of claim 13 further comprising:
c) preparing the 5'-diacyl glycerophosphate of said 2' modified pyrimidine.

16. The method of claim 12 further comprising:
preparing an oligonucleotide comprising at least one of said 2' modified pyrimidines.

17. A modified pyrimidine compound having the formula:

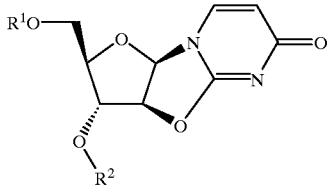

wherein $R^1$ is H or an alcohol protecting group, and $R^2$ is selected from the group consisting of —C(O)NHOTBDMS,

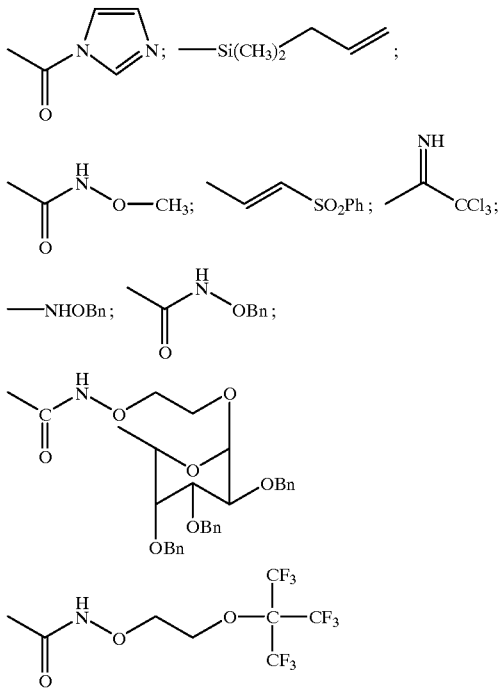

18. A 2' modified nucleoside having the formula:

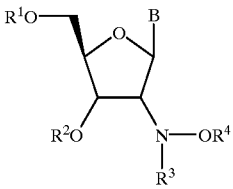

wherein
B is a pyrimidine or a purine, $R^1$ and $R^2$ are independently selected from the group consisting of H, an alcohol protecting group, a phosphoramidite, a triphosphate or a diacyl glycerophosphate, $R^3$ is H, alkyl, alkenyl, aryl, oligoethylene glycol or benzoyl, and $R^4$ is H, alkyl, alkenyl, aryl, silyl protecting group, oligoethylene glycol or benzoyl.

19. The 2' modified nucleoside of claim 18 wherein $R^4$ is selected from the group consisting of $CH_3$, Bn and TBDMS and $R^3$ is $CH_3$.

20. An oligonucleotide comprised of at least one residue of a compound of the formula:

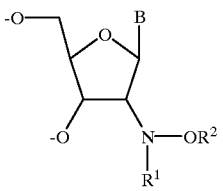

wherein B is a pyrimidine or a purine, $R^1$ is selected from H, alkyl, alkenyl, aryl, oligoethylene glycol or benzoyl, and $R^2$ is selected from H, alkyl, alkenyl, aryl, silyl protecting group, oligoethylene glycol or benzoyl.

21. A 2' modified nucleoside having the formula:

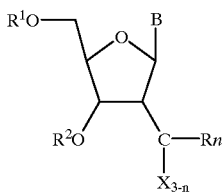

wherein B is a pyrimidine or purine, $R^1$ and $R^2$ are independently selected from the group consisting of H, an alcohol protecting group, a phosphoramidite, a triphosphate or a diacyl glycerophosphate, X is selected from the group consisting of F, Cl, Br and I, R is selected from the group consisting of H and substituted or unsubstituted alkyl, and n is 0–3.

22. A 3'-phosphoramidite of a 2' modified nucleoside of claim 21.

23. A 5'-triphosphate of a 2' modified nucleoside of claim 21.

24. A 5'-diacyl glycerophosphate of a 2' modified nucleoside of claim 21.

25. An oligonucleotide comprised of at least one residue of the 2' modified nucleoside of claim 21.

26. A compound having the formula:

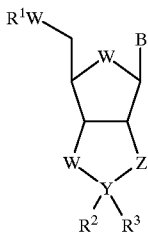

wherein
B is a nucleobase;
W is independently selected from the group consisting of O and S;
Y is selected from the group consisting of a metal, C, Si, Se, S, B, and P;
Z is selected from the group consisting of Cl, F, H, $^2H$, $^3H$, OH, $NHOR^1$, $NHOR^5$, $NHNHR^5$, $NHR^5$, =NH, CHCN, $CHCl_2$, SH, $CFH_2$, $CF_2H$, $CR^2_2$, $OR^4$, $CHR^2$;
$R^1$ is selected from the group consisting of H and an alcohol protecting group;
$R^2$ is selected from the group consisting of =O, =S, H, OH, $CCl_3$, $CF_3$, halide, optionally substituted $C_1$–$C_{20}$ alkyl, alkenyl, aryl, $C_1$–$C_{20}$ carbonyl, $C_1$–$C_{20}$ acyl, benzoyl, $OR^4$ and esters;
$R^3$ is selected from the group consisting of OH, H, $CCl_3$, $CF_3$, halide, $C_1$–$C_{20}$ alkyl, alkenyl, aryl, benzoyl, esters, $OR^4$ and omitted as a variable when $R^2$ is =O or =S;
$R^4$ is selected from the group consisting of an optionally substituted $C_1$–$C_{20}$ alkyl, $C_2$–$C_{20}$ alkenyl, $C_2$–$C_{20}$ alkynyl, and aryl, and phosphate; and
$R^5$ is selected from the group consisting of $R^2$, $R^4$, CN, $C(O)NH_2$, peptide and $C(S)NH_2$.

27. The compound of claim 26 wherein:
B is selected from the group consisting of a pyrimidine connected to X at the 2-position, a pyrimidine connected to X at the 6-position, and a purine connected to X at the 8-position;
W is O
Y is selected from the group consisting of a metal, C, Si, B, and P;
Z is selected from the group consisting of imidazole, H, $NHOR^1$, $NHOR^5$, $NHNHR^2$, $NHR^2$, =NH, SH, and $OR^4$;
$R^1$ is selected from the group consisting of H and an alcohol protecting group;
$R^2$ is selected from the group consisting of =O, =S, OH, H, $CCl_3$, $CF_3$, halide, $C_1$–$C_{20}$ alkyl, alkenyl, aryl, $C_1$–$C_{20}$ acyl, benzoyl, and ester;
$R^3$ is selected from the group consisting of H, $CCl_3$, $CF_3$, halide, $C_1$–$C_{20}$ alkyl, alkenyl, aryl, benzoyl, esters and omitted as a variable when $R^2$ is =O or =S;
$R^4$ is selected from the group consisting of optionally substituted $C_1$–$C_{20}$ alkyl, $C_2$–$C_{20}$ alkenyl, $C_2$–$C_{20}$ alkynyl, and aryl; and
$R^5$ is selected from the group consisting of $R^2$, $R^4$ and peptide.

28. A compound having the formula:

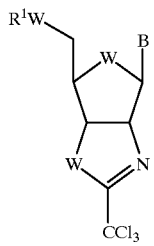

wherein B is a pyrimidine or purine; W is selected from the group consisting of S, O, $CH_2$, and N; and $R^1$ is H or an alcohol protecting group.

29. A method for the stereospecific reduction of the 2'-position of 2,2' anhydropyrimidine comprising: performing the intramolecular introduction of a substituent to the 2' position of a 2,2' ambydropyrimidine via an activatable 3+ substituent wherein said activatable 3' substituent is reducing agent, and isolating said stereospecifically reduced pyrimidine.

30. A process for preparing a compound having the formula:

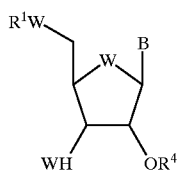

comprising:

a) reacting a compound having the formula

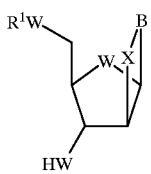

with a metal alkoxide, M(OR$^4$)$_n$, wherein
R$^1$ is selected from the group consisting of H and an alcohol protecting group;
W is independently selected from the group consisting of S and O;
X is selected from the group consisting of O, S, NH, and NR$^4$;
B is a nucleobase;
R$^2$ is selected from the group consisting of =O, =S, H, OH, CCl$_3$, CF$_3$, halide, optionally substituted C$_1$–C$_{20}$ alkyl, alkenyl, aryl, C$_1$–C$_{20}$acyl, benzoyl, OR$^4$ and esters;
R$^4$ is selected from the group consisting of optionally substituted hydrocarbon (C$_{1-19}$) alkyl, alkenyl, alkynyl, aryl, and phosphate;
M is a metal capable of forming a bis or higher alkoxide with OR$^4$ selected from the group consisting of Mg, Be, Sr, Ba, Th, Zr, Cr, Fe, Ni, Cu, Zn, Mn, Ca, Ce, Ti, Si, Sn, Pd, and the lanthanide series; and
n is 2–6.

31. The process of claim 30 wherein M is selected from the group consisting of calcium, magnesium or cerium.

32. The process of claim 30 wherein B is selected from the group consisting of uracil, cytosine, guanine, and adenine.

33. The process of claim 30 wherein B is a pyrimidine.

34. The process of claim 30 wherein R$^1$ is selected from the group consisting of dimethoxytrityl or t-butyldipheny silyl.

35. The process of claim 30 wherein R$^4$ is selected from the group consisting of methyl, ethyl, propyl, allyl, butyl, and pentyl.

36. The process of claim 30 wherein W and X are both O.

37. The process of claim 30 wherein X is S.

38. The process of claim 37 which further comprises:
b) desulfurizing the compound with a desulfurizing reagent.

39. The process of claim 37 wherein B is a purine.

40. The process of claim 37 wherein B is an N-protected guanine or adenine.

41. The process of claim 37 wherein B is 2,6-diaminopurine.

42. The process of claim 30 wherein the metal alkoxide used is magnesium methoxide.

43. A compound prepared according to the method comprising:
a) performing the intramolecular nucleophilic reaction of an intermediate compound having the formula:

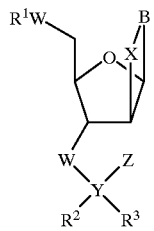

wherein
B is a nucleobase;
W is independently selected from the group consisting of S, CR$^2$$_2$, and NR$^2$;
X is selected from the group consisting of O, S, NH, and NR$^4$;
Y is selected from the group consisting of a metal, C, Si, Se, S, B, and P;
Z is selected from the group consisting of imidazole, Cl, F, H, $^2$H, $^3$H, OH, NHOR$^1$, NHOR$^5$, NHNHR$^5$, =NH, NHR$^5$,CHCN, CHCl$_2$, SH, SR$^5$, CFH$_2$, CF$_2$H, CR$^2$$_2$Br, OR$^4$;
R$^1$ is selected from the group consisting of H and an alcohol protecting group;
R$^2$ is selected from the group consisting of =O, =S, H, OH, CCl$_3$, CF$_3$, halide, optionally substituted C$_1$–C$_{20}$ alkyl, alkenyl, aryl, C$_1$–C$_{20}$acyl, benzoyl, OR$^4$ and esters;
R$^3$ is selected from the group consisting of OH, H, CCl$_3$, CF$_3$, halide, C$_1$–C$_{20}$ alkyl, alkenyl, aryl, benzoyl, esters, OR$^4$, omitted as a variable when R$^2$ is =O or =S, and cyclopentadiene, cyclooctadiene, CO, trialkylphosphines if Y is metal;
R$^4$ is selected from the group consisting of an optionally substituted C$_1$–C$_{20}$ alkyl, C$_2$–C$_{20}$ alkenyl, C$_2$–C$_{20}$ alkynyl, and aryl and phosphate;
R$^5$ is selected from the group consisting of R$^2$, R$^4$, CN, C(O)NH$_2$, C(S)NH$_2$ and SO$_2$R$^4$ in the presence of a base; and b) isolating said compound.

44. The compound of claim 43, wherein said method further comprises:
c) preparing the 3'-phosphoramidite of said compound.

45. The compound prepared according to the method of claim 43, wherein said method further comprises:
c) preparing the 5'-triphosphate of said compound.

46. The compound prepared according to the method of claim 43, wherein said method further comprises:
c) preparing the 5'-diacylglycerophosphate of said compound.

47. A compound prepared according to the method comprising:
a) performing the intramolecular nucleophilic reaction of an intermediate compound having the formula:

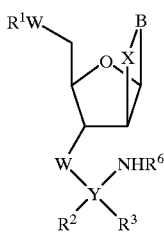

wherein

B is a nucleobase;

W is S;

X is selected from the group consisting of O, S, NH, and $NR^4$;

Y is selected from the group consisting of a metal, C, Si, Se, S, B, and P;

$R^1$ is selected from the group consisting of H and an alcohol protecting group;

$R^2$ is selected from the group consisting of =O, =S, H, OH, $CCl_3$, $CF_3$, halide, optionally substituted $C_1-C_{20}$ alkyl, alkenyl, aryl, $C_1-C_{20}$ acyl, benzoyl, $OR^4$ and esters;

$R^3$ is selected from the group consisting of OH, H, $CCl_3$, $CF_3$, halide, $C_1-C_{20}$ alkyl, alkenyl, aryl, benzoyl, esters, $OR^4$, omitted as a variable when $R^2$ is =O or =S, and cyclopentadiene, cyclooctadiene, CO, trialkylphosphines if Y is metal;

$R^4$ is selected from the group consisting of an optionally substituted $C_1-C_{20}$ alkyl, $C_2-C_{20}$ alkenyl, $C_2-C_{20}$ alkynyl, and aryl, alcohol protecting group and phosphate;

$R^5$ is selected from the group consisting of $R^2$, $R^4$, CN, $C(O)NH_2$, $C(S)NH_2$ and $SO_2R^4$ $R^6$ is selected from the group consisting of $OR^7$, $CCl_3$, $CF_3$, optionally substituted ($C_1-C_{20}$ alkyl, $C_2-C_{20}$ alkenyl, $C_2-C_{20}$ alkynyl, and aryl), benzoyl, esters, CN, $C(O)NH_2$, $C(S)NH_2$, $OR^4$, carbonyl, thiocarbonyl and $SO_2R^4$;

$R^7$ is selected from the group consisting of $CCl_3$, $CF_3$, optionally substituted $C_1-C_{20}$ alkyl, $C_2-C_{20}$ alkenyl, $C_2-C_{20}$ alkynyl, and aryl, benzoyl, esters, $C(O)NH_2$, $C(S)NH_2$, and $SO_2R^4$; in the presence of a base; and b) isolating said compound.

48. A 3'-phosphoramidite of the compound of claim 47.

49. A 5'-triphosphate of the compound of claim 47.

50. A 5'-diacylglycerophosphate of the compound of claim 47.

51. A 2' modified nucleoside having the formula:

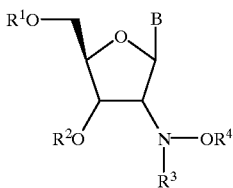

wherein

B is a pyrimidine or a purine, $R^1$ and $R^2$ are H or an alcohol protecting group, $R^3$ is H and $R^4$ is alkyl, alkenyl, aryl, oligoethylene glycol or benzoyl.

52. A 3'-phosphoramidite of a 2' modified nucleoside of claim 51.

53. A 5'-triphosphate of the 2' modified nucleoside of claim 51.

54. A 5'-diacyl glycerophosphate of the 2' modified nucleoside of claim 51.

55. An oligonucleotide comprised of at least one residue of the 2' modified nucleoside of claim 51.

56. The method of claims 1 or 2 wherein said metal is selected from Al of Sn.

57. The compound of claims 8, 26, 27, 43 or 47 wherein said metal is selected from Al or Sn.

58. A 2' modified nucleoside prepared according to the method comprising:

a) performing the intramolecular nucleophilic reaction of an intermediate compound having the formula:

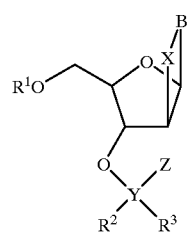

wherein

B is a nucleobase;

X is selected from the group consisting of S, NH, and $NR^4$;

Y is selected from the group consisting of a metal, C, Si, Se, S, B, and P;

Z is selected from the group consisting of imidazole, Cl, F, F, H, $^2H$, $^3H$, OH, $NHOR^1$, $NHOR^5$, $NHNHR^5$, $NHR^5$, =NH, CHCN, $CHCl_2$, SH, $SR^5$, $CFH_2$, $CF_2H$, $CR^2_2Br$, $OR^4$;

$R^1$ is selected from the group consisting of H and an alcohol protecting group;

$R^2$ is selected from the group consisting of =O, =S, H, OH, $CCl_3$, $CF_3$, halide, optionally substituted $C_1-C_{20}$ alkyl, alkenyl, aryl, $C_1-C_{20}$ acyl, benzoyl, $OR^4$ and esters;

$R^3$ is selected from the group consisting of OH, H, $CCl_3$, $CF_3$, halide, $C_1-C_{20}$ alkyl, alkenyl, aryl, benzoyl, esters, $OR^4$, omitted as a variable when $R^2$ is =O or =S, and cyclopentadiene, cyclooctadiene, CO, trialkylphosphines if Y is metal;

$R^4$ is selected from the group consisting of an optionally substituted $C_1-C_{20}$ alkyl, $C_2-C_{20}$ alkenyl, $C_2-C_{20}$ alkynyl, and aryl and phosphate;

$R^5$ is selected from the group consisting of $R^2$, $R^4$, CN, $C(O)NH_2$, $C(S)NH_2$ and $SO_2R^4$ in the presence of a base; and b) isolating said 2' modified nucleoside.

59. The method of claim 65 wherein said metal is selected from Al or Sn.

60. A 2' modified nucleoside prepared according to the method comprising:

a) performing the intramolecular nucleophilic reaction of an intermediate compound having the formula:

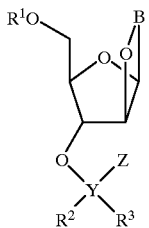

wherein

B is a nucleobase;

Y is selected from the group consisting of a metal, C, Si, Se, S, B, and P;

Z is selected from the group consisting of imidazole, F, $^2$H, $^3$H, NHNHR$^5$, =NH, CHCN, CHCl$_2$, SR$^5$, CF$_2$H, CR$^2{}_2$Br, OR$^4$;

R$^1$ is selected from the group consisting of H and an alcohol protecting group;

R$^2$ is selected from the group consisting of =O, =S, H, OH, CCl$_3$, CF$_3$, halide, optionally substituted C$_1$–C$_{20}$ alkyl, alkenyl, aryl, C$_1$–C$_{20}$ acyl, benzoyl, OR$^4$ and esters;

R$^3$ is selected from the group consisting of OH, H, CCl$_3$, CF$_3$, halide, C$_{1-20}$ alkyl, alkenyl, aryl, benzoyl, esters, OR$^4$, omitted as a variable when R$^2$ is =O or =S, and cyclopentadiene, cyclooctadiene, CO, trialkylphosphines if Y is metal;

R$^4$ is selected from the group consisting of an optionally substituted C$_1$–C$_{20}$ alkyl, C$_2$–C$_{20}$ alkenyl, C$_2$–C$_{20}$ alkynyl, and aryl and phosphate;

R$^5$ is selected from the group consisting of R$^2$, R$^4$, CN, C(O)NH$_2$, C(S)NH$_2$ and SO$_2$R$^4$ in the presence of a base; and b) isolating said 2' modified nucleoside.

61. The method of claim 60 wherein said metal is selected from Al or Sn.

62. An oligonucleotide comprising at least one nucleotide prepared according to the method comprising:

a) performing the intramolecular nucleophilic reaction of an intermediate compound having the formula:

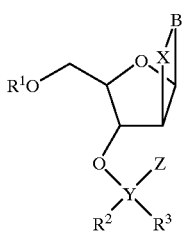

wherein

B is a nucleobase;

X is selected from the group consisting of S, NH, and NR$^4$;

Y is selected from the group consisting of a metal C, Si, Se, S, B, and P;

Z is selected from the group consisting of imidazole, Cl, F, F, H, $^2$H, $^3$H, OH, NHOR$^1$, NHOR$^5$, NHNHR$^5$, NHR$^5$, =NH, CHCN, CHCl$_2$, SH, SR$^5$, CFH$_2$, CF$_2$H, CR$^2{}_2$Br, OR$^4$;

R$^1$ is selected from the group consisting of H and an alcohol protecting group;

R$^2$ is selected from the group consisting of =O, =S, H, OH, CCl$_3$, CF$_3$, halide, optionally substituted C$_1$–C$_{20}$ alkyl, alkenyl, aryl, C$_1$–C$_{20}$ acyl, benzoyl, OR$^4$ and esters;

R$^3$ is selected from the group consisting of OH, H, CCl$_3$, CF$_3$, halide, C$_1$–C$_{20}$ alkyl, alkenyl, aryl, benzoyl, esters, OR$^4$, omitted as a variable when R$^2$ is =O or =S, and cyclopentadiene, cyclooctadiene, CO, trialkylphosphines if Y is metal;

R$^4$ is selected from the group consisting of an optionally substituted C$_1$–C$_{20}$ alkyl, C$_2$–C$_{20}$ alkenyl, C$_2$–C$_{20}$ alkynyl, and aryl and phosphate; and R$^5$ is selected from the group consisting of R$^2$, R$^4$, CN, C(O)NH$_2$, C(S)NH$_2$ and SO$_2$R$^4$ in the presence of a base.

63. An oligonucleotide comprising at least one nucleotide prepared according to the method comprising:

a) performing the intramolecular nucleophilic reaction of an intermediate compound having the formula:

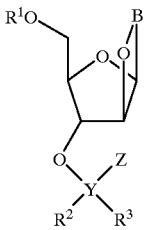

wherein

B is a nucleobase;

Y is selected from the group consisting of a metal, C, Si, Se, S, B, and P;

Z is selected from the group consisting of imidazole, F, $^2$H, $^3$H, NHNHR$^5$, =NH, CHCN, CHCl$_2$, SR$^5$, CF$_2$H, CR$^2{}_2$Br, OR$^4$;

R$^1$ is selected from the group consisting of H and an alcohol protecting group;

R$^2$ is selected from the group consisting of =O, =S, H, OH, CCl$_3$, CF$_3$, halide, optionally substituted C$_1$–C$_{20}$ alkyl, alkenyl, aryl, C$_1$–C$_{20}$ acyl, benzoyl, OR$^4$ and esters;

R$^3$ is selected from the group consisting of OH, H, CCl$_3$, CF$_3$, halide, C$_1$–C$_{20}$ alkyl, alkenyl, aryl, benzoyl, esters, OR$^4$, omitted as a variable when R$^2$ is =O or =S, and cyclopentadiene, cyclooctadiene, CO, trialkylphosphines if Y is metal;

R$^4$ is selected from the group consisting of an optionally substituted C$_1$–C$_{20}$ alkyl, C$_2$–C$_{20}$ alkenyl, C$_2$–C$_{20}$ alkynyl, and aryl and phosphate; and R$^5$ is selected from the group consisting of R$^2$, R$^4$, CN, C(O)NH$_2$, C(S)NH$_2$ and SO$_2$R$^4$ in the presence of a base.

64. A method for the synthesis of 2' modified nucleosides which comprises:

a) performing the intramolecular nucleophilic reaction of an intermediate compound having the formula:

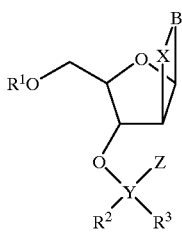

wherein

B is a nucleobase;

X is selected from the group consisting of O, S, NH, and $NR^4$;

Y is selected from the group consisting of a metal, C, Si, Se, S, B, and P;

Z is selected from the group consisting of imidazole, Cl, F, H, $^2$H, $^3$H, OH, $NHOR^1$, $NHOR^5$, $NHNHR^5$, $NHR^5$, =NH, CHCN, $CHCl_2$, SH, $SR^5$, $CFH_2$, $CF_2H$, $CR^2{}_2Br$, $OR^4$;

$R^1$ is selected from the group consisting of H and an alcohol protecting group;

$R^2$ is selected from the group consisting of =O, =S, H, OH, $CCl_3$, $CF_3$, halide, optionally substituted $C_1$–$C_{20}$ alkyl, alkenyl, aryl, $C_1$–$C_{20}$ acyl, benzoyl, $OR^4$ and esters;

$R^3$ is selected from the group consisting of OH, H, $CCl_3$, $CF_3$, halide, $C_1$–$C_{20}$ alkyl, alkenyl, aryl, benzoyl, esters, $OR^4$, omitted as a variable when $R^2$ is =O or =S, and cyclopentadiene, cyclooctadiene, CO, trialkylphosphines if Y is metal;

$R^4$ is selected from the group consisting of an optionally substituted $C_1$–$C_{20}$ alkyl, $C_2$–$C_{20}$ alkenyl, $C_2$–$C_{20}$ alkynyl, aryl, and phosphate;

$R^5$ is selected from the group consisting of $R^2$, $R^4$, CN, $C(O)NH_2$, $C(S)NH_2$, and $SO_2R^4$, in the presence of a base; and b) isolating said 2' modified nucleoside.

65. The method of claim 64 further comprising:

c) preparing an oligonucleotide comprising at least one of said 2' modified nucleosides.

* * * * *